United States Patent
Singh et al.

(10) Patent No.: US 7,128,928 B2
(45) Date of Patent: Oct. 31, 2006

(54) OPHTHALMIC FORMULATION WITH NOVEL GUM COMPOSITION

(75) Inventors: Satish K. Singh, Portage, MI (US); Paramita Bandyopadhyay, Portage, MI (US)

(73) Assignee: Pharmacia Corporation, Peapack, NJ (US)

( * ) Notice: Subject to any disclaimer, the term of this patent is extended or adjusted under 35 U.S.C. 154(b) by 555 days.

(21) Appl. No.: 10/370,220

(22) Filed: Feb. 20, 2003

(65) Prior Publication Data

US 2003/0232089 A1 Dec. 18, 2003

Related U.S. Application Data

(60) Provisional application No. 60/358,761, filed on Feb. 22, 2002.

(51) Int. Cl.
- A61F 2/00 (2006.01)
- A61K 31/74 (2006.01)
- A61K 9/14 (2006.01)

(52) U.S. Cl. .............. 424/427; 424/78.04; 424/488

(58) Field of Classification Search ........... 424/488, 424/426, 427, 428, 78.04
See application file for complete search history.

(56) References Cited

U.S. PATENT DOCUMENTS

| | | | |
|---|---|---|---|
| 4,136,173 A | 1/1979 | Pramoda et al. | 424/177 |
| 4,136,177 A | 1/1979 | Lin et al. | 424/211 |
| 4,136,178 A | 1/1979 | Lin et al. | 424/211 |
| 4,642,305 A * | 2/1987 | Johansson et al. | 514/182 |
| 4,676,976 A | 6/1987 | Toba et al. | |
| 4,727,064 A | 2/1988 | Pitha | 514/58 |
| 4,844,902 A | 7/1989 | Grohe | 424/449 |
| 4,861,760 A | 8/1989 | Mazuel et al. | 514/54 |
| 5,134,127 A | 7/1992 | Stella et al. | 514/58 |
| 5,135,920 A | 8/1992 | Kanamaru et al. | 514/59 |
| 5,212,162 A | 5/1993 | Missel et al. | 514/54 |
| 5,227,372 A | 7/1993 | Folkman | 514/58 |
| 5,369,095 A | 11/1994 | Kee et al. | 514/24 |
| 5,376,645 A | 12/1994 | Stella et al. | 514/58 |
| 5,403,841 A | 4/1995 | Lang et al. | 514/226.8 |
| 5,521,222 A | 5/1996 | Ali et al. | 514/772.5 |
| 5,688,791 A | 11/1997 | Kimura et al. | 514/224.5 |
| 5,710,182 A | 1/1998 | Reunamäki et al. | 514/772.3 |
| 5,776,445 A | 7/1998 | Cohen et al. | 424/78.04 |
| 5,795,913 A | 8/1998 | Lehmussaari et al. | 514/459 |
| 5,837,870 A | 11/1998 | Pearlman et al. | 544/137 |
| 5,874,418 A | 2/1999 | Stella et al. | 514/58 |
| 5,888,493 A | 3/1999 | Sawaya | 424/78.04 |
| 5,958,443 A | 9/1999 | Viegas et al. | |

(Continued)

FOREIGN PATENT DOCUMENTS

EP 0 149 197 7/1985

(Continued)

OTHER PUBLICATIONS

PCT International Search Report, PCT/US03/05361.

(Continued)

*Primary Examiner*—Sharon Kennedy
(74) *Attorney, Agent, or Firm*—Edward D. Robinson; Bryan C. Zielinski

(57) ABSTRACT

There is provided a pharmaceutical composition suitable for topical administration to an eye, the composition comprising (a) a pharmacologically effective concentration of an active agent and (b) a combination of at least two ophthalmically compatible polymers comprising a novel gum system. In preferred embodiments of the present invention, the compositions increase the retention time of the active agent in the eye, when compared to compositions with other gums or gum systems.

24 Claims, 20 Drawing Sheets

U.S. PATENT DOCUMENTS

| | | | |
|---|---|---|---|
| 5,985,259 A | 11/1999 | Cagle et al. | 424/78.04 |
| 6,046,177 A | 4/2000 | Stella et al. | 514/58 |
| 6,133,248 A | 10/2000 | Stella | 514/58 |
| 6,162,449 A * | 12/2000 | Maier et al. | 424/401 |
| 6,174,524 B1 | 1/2001 | Bawa et al. | 424/78.04 |
| 6,224,905 B1 | 5/2001 | Lawrence et al. | 424/464 |
| 6,290,729 B1 | 9/2001 | Slepian et al. | 623/23.72 |
| 6,551,584 B1 * | 4/2003 | Bandyopadhyay et al. | 424/78.04 |
| 2002/0107238 A1 * | 8/2002 | Bandyopadhyay et al. | 514/211.15 |

FOREIGN PATENT DOCUMENTS

| | | |
|---|---|---|
| EP | 0 312 208 | 4/1989 |
| EP | 0 424 043 | 4/1991 |
| EP | 0 590 655 | 4/1994 |
| EP | 0 642 334 | 3/1995 |
| EP | 0 891 768 A | 1/1999 |
| EP | 0 938 903 | 9/1999 |
| JP | 06 345653 A | 8/1993 |
| WO | WO 93/17664 | 9/1993 |
| WO | WO 97/10805 | 3/1997 |
| WO | WO 98/47535 | 10/1998 |
| WO | WO 99/24393 | 10/1998 |
| WO | WO 99/06023 | 2/1999 |
| WO | WO 99/24393 | 5/1999 |
| WO | WO 99/43333 | 9/1999 |
| WO | WO 00/42992 | 7/2000 |
| WO | WO 01/01950 | 1/2001 |
| WO | WO 01/19366 | 3/2001 |
| WO | WO 01/96461 | 12/2001 |

OTHER PUBLICATIONS

Asahi Kasei Kogyo KK, Database WPI, Section Ch., Week 199510, Derwent Publications Ltd., London, GB, Class A96, AN 1995-070221, abstract.

Bekers et al., (1991), Cyclodextrins in the Pharmaceutical Field, *Drug Development and Industrial Pharmacy*, 17(11), pp. 1503-1549.

Cohen et al., (1997), A Novel in situ-forming ophthalmic drug delivery system from alginates undergoing gelation in the eye, *Journal of Controlled Release*, 44, pp. 207-208.

Le Bourlais et al., (1998), Ophthalmic Drug Delivery Systems—Recent Advances, *Progress in Retinal & Eye Research*, vol. 17, No. 1, pp. 33-58.

Loftsson, (1998), Increasing the cyclodextrin complexation of drugs and drug bioavailability through addition of water-soluble polymers, *Pharmazie*, 53, 11, pp. 733-740.

Szejtli, (1994), Medicinal Applications of Cyclodextrins, *Medicinal Research Reviews*, vol. 14, No. 3, pp. 353-386.

Zhang & Rees, (1999), A review of recent applications of cyclodextrins for drug delivery, *Expert Opinion on Therapeutic Patents*, 9, pp. 1697-1717.

* cited by examiner

OPHTHALMIC FORMULATION WITH NOVEL GUM COMPOSITION

The present application claims the benefit of U.S. Provisional Application No. 60/358,761, filed on Feb. 22, 2002.

FIELD OF THE INVENTION

The present invention relates to a pharmaceutical composition in an aqueous solution form useful for administration of an active agent to an eye of a subject. In particular, the present invention relates to such a composition containing novel combinations of viscosity enhancers or gel-forming agents that increase retention time of the composition in an eye, after administration thereto. The field of the present invention also include use of such a composition for treatment or prevention of disease or infection of the eye, for amelioration of symptoms of dry eye, and use of such a formulation in preparation of a medicament.

BACKGROUND OF THE INVENTION

A major problem encountered with topical delivery of ophthalmic drugs is the rapid and extensive precorneal loss caused by drainage and high tear fluid turnover. After instillation of an eye-drop, typically less than 5% of the applied drug penetrates the cornea and reaches intraocular tissues. After topical administration of an ophthalmic drug solution, the drug is first diluted by the lacrimal fluid. The contact time of drug with ocular tissue is relatively short (1–2 min) because of the permanent production of lacrymal fluid (0.5–2.2 μL/min). Then, approximately half of the drug flows through the upper canaliculus and the other half, through the lower canaliculus into the lacrimal sac, which opens into the nasolacrimal duct. Drainage of lacrymal fluid during blinking (every 12 s) towards the nasolacrimal duct induces a rapid elimination of the dose.

Several different approaches have been attempted in order to overcome the disadvantages of solution-based eye-drops, outlined above. Specifically, various ophthalmic delivery systems, such as hydrogels, micro-and nanoparticles, liposomes, and inserts have all been investigated. Most of the formulation efforts have been aimed at maximizing ocular drug absorption through prolongation of the drug residence time in the cornea and conjunctival sac. Control of residence time has been accomplished to a minimal extent through the use of viscosifying agents added to aqueous solution, and to a greater extent, through the use of diffusion-controlled, non-erodible polymeric inserts (e.g. Ocusert®, a trademark of Alza Corp.) This last solution has not been very successful because of a low degree of patient compliance, due to irritation, difficulty in insertion, and over-extended retention.

Viscosified solutions or gels have been accepted to a greater degree by patients, among other things, because of the ease of administration, lack of irritation of the eye as a result of administration thereto, and lower cost compared to other treatment methods. However, existing formulations of viscosified solutions only increase residence time of a drug in the eye to a limited extent, so the same solution must be applied to an eye multiple times to treat or prevent a given illness or infection of the eye. Many of the marketed ophthalmic formulations currently use the polymers hydroxypropyl methylcellulose, hydroxyethyl cellulose, and polyvinyl alcohol to increase the viscosity of the formulation. Other viscosity enhancers disclosed as being suitable for use in ophthalmic formulations include, but are not limited to propylene glycol alginate (U.S. Pat. No. 4,844,902; U.S. Pat. No. 5,776,445), tragacanth (U.S. Pat. No. 5,369,095).

A basic and important characteristic of the systems described immediately above is their viscosity. However, simply enhancing the viscosity of an ophthalmic formulation is not sufficient. Pseudo-plastic formulations that show a reduced viscosity upon shear are of great interest since such formulations support ocular movement and blinking leading to greater acceptability than simple viscous Newtonian formulations. Shear rates associated with normal blinking range from 0 at rest to 10,000 $s^{-1}$ during blinking. Gel systems exhibiting critical yield behavior below these shear rates are also comfortable when dosed.

A degree of mucoadhesivity is also advantageous in such systems. The best bioadhesive polymers have been found to be polyanions such as polyacrylic acid.

A variation of viscosified solutions has been the use of in-situ gelling systems which have the advantage that the formulation is easy to instill due to its fluid nature, but the in-situ gelling ability allows for increased retention in the eye. Gelling occurs as a result of ion concentration change or temperature change. Examples of polymers incorporated into ophthalmic formulations to promote in situ gelling include, but are not limited to, xanthan gum (U.S. Pat. No. 6,174,524 B1), xanthan gum and locust bean gum (See U.S. Pat. Nos. 4,136,173; 4,136,177; and 4,136,178), gellan gum (U.S. Pat. No. 4,861,760), carageenans (EP 0 424 043 A1; U.S. Pat. No. 5,403,841), cellulose and derivatives thereof including Carbopol® (trademark of B.F. Goodrich) (U.S. Pat. No. 5,888,493 and U.S. Pat. No. 5,710,182), hydroxypropyl guar (WO 99/06023), pectin (EP 0 312 208; WO 98/47535), and a sulfated glucan sulfate such as $\beta$-1,3-glucan sulfate (U.S. Pat. No. 5,227,372; U.S. Pat. No. 5,135,920).

A limited number of combinations of gels have also been disclosed as being suitable for use in ophthalmic formulations. For example, U.S. Pat. No. 5,212,162 indicates that one could use "xanthan gum, locust bean gum, gellan gum, carrageenens, and combinations thereof." (col. 2, lines 11–14). However, no examples of even a single formulation containing any such combination is provided therein. The only examples illustrated the manufacture and use of formulations containing only a single species of gum per solution. Therefore, it is unclear, from that patent, whether any such combinations would actually work.

WO 01/96461 discloses fluid gels of xanthan and non-gelling polysaccharides, such as konjac mannan, tara, locust bean, and guar gum for use in a variety of different cosmetic applications (e.g. in a bath gel, a shower gel, a shampoo, an antiperspirant, a face mask, etc.). However, that international application publication does not suggest that particular combination would be suitable for use in an ophthalmic formulation or method of application of an active agent to an eye.

A summary of the viscosified/bioadhesive and in-situ gelling systems can also be found in Le Bourlais et al, *Progr. Retinal & Eye Res.* 17: 33–58 (1998).

There remains a need for simple, low cost ophthalmic formulations that provide enhanced viscosity and/or gel forming capability in the eye than is possible with existing formulations. The present ophthalmic formulations and gum systems meet the needs discussed above, as becomes apparent from the description and illustration of the present invention, below.

SUMMARY OF THE INVENTION

The present invention provides a pharmaceutical composition suitable for topical administration to an eye, comprising an active agent and a novel gum system. In one embodiment of the present invention, the novel gum system comprises a set of at least two ophthamalogically compatible polymers selected from the group consisting of konjac, scleroglucan, hydroxypropyl guar, propylene glycol alginate, sodium alginate, Carbopol 971, pectin, and agarose. In another embodiment, the novel gum system is a combination of xanthan and alginate. In yet another embodiment, the novel gum system is a combination of xanthan and konjac. In yet another embodiment, the novel gum system is a combination of xanthan and citrus pectin. When the active agent is poorly soluble in the composition, the composition preferably further includes a solubilizing agent, such as an ophthalmically acceptable cyclodextrin compound.

In another embodiment, the present invention is directed to a pharmaceutical composition for topical administration to an eye, comprising: an oxazolidinone antimicrobial drug in a concentration effective for treatment and/or prophylaxis of a gram-positive bacterial infection of at least one tissue of the eye, an ophthalmically acceptable cyclodextrin compound in a concentration sufficient to maintain the oxazolidinone antibiotic drug in solution, and a novel gum system as described immediately above.

The reason for including a cyclodextrin in either of these last two embodiments of the present invention is not to be viewed as a restriction of the invention. The cyclodextrin compound can be included for any one of a number of different reasons, including but not limited to reducing solubilization, reducing irritation, enhancing permeation, and enhancing stability.

It is believed, without being bound by theory, that the enhanced solubility of active agents in the presence of a cyclodextrin in some of the embodiments of the present composition described above is due to association of at least a portion of the active agent with the cyclodextrin. It is further believed that at least one mechanism by which the active agent associates with the cyclodextrin compound to enhance solubility of the drug in an aqueous medium is through formation of an inclusion complex. Such complexes or conjugates are known in the art to form with a variety of drugs, and a number of advantages have been postulated for use of cyclodextrin-drug complexes in pharmacy. See for example review articles by Bekers et al. (1991) in *Drug Development and Industrial Pharmacy*, 17, 1503–1549; Szejtli (1994) in *Medical Research Reviews*, 14, 353–386; and Zhang & Rees (1999) in *Expert Opinion on Therapeutic Patents*, 9, 1697–1717.

Specifically, derivatives of cyclodextrin, including $\alpha$-, $\beta$, and $\gamma$-cyclodextrins and derivatives thereof, such as ether and mixed ether derivatives, and derivatives bearing sugar residues have been disclosed as being suitable for use in the solubilization of various drugs that are only sparingly soluble in water. EP 0149 197 B2 (Canadian counterpart, CA 1222697) discloses the suitability of partially etherified $\beta$-cyclodextrin and derivatives thereof, including hydroxyethyl, hydroxypropyl, and hydroxypropyl-methyl-$\beta$ cyclodextrin for the solubilization of various types of drugs which are instable or only sparingly soluble in water. None of the drugs disclosed by EP 0149 197 B2 as having been solubilized with one or more of the partially etherified $\beta$-cyclodextrins was an antibiotic, much less an oxazolidinone. Likewise, U.S. Pat. No. 4,727,064 discloses the use of hydroxypropyl-$\beta$-cyclodextrin and the use of mixtures of that cyclodextrin derivative, diethylaminoethyl-$\beta$-cyclodextrin, carboxymethyl-$\beta$-cyclodextrin, and carboxamidomethyl-$\beta$-cyclodextrin to assist in the dissolution of drugs, but does not disclose the solibilization of any oxazolidinone using such a solubility enhancer. Various sulfoalkyl ether cyclodextrin derivatives, including sulfobulylether-$\beta$-cyclodextrin, and their utility in solubilizing certain active agents are disclosed in U.S. Pat. Nos. 5,134,127; 5,376,645. Uses of such sulfoalkyl ether cyclodextrin derivatives in solubilizing additional active agents are disclosed in U.S. Pat. Nos. 5,134,127, 5,874,418; 6,046,177; and 6,133,248.

For general patents disclosing the solubilization of various types of drugs by cyclodextrin compounds, see U.S. Pat. No. 4,727,064 to Pitha, EP 0 149 197 B2 by JANSSEN PHARMACEUTICA N.V., Janssen application). This enhancement in solubility, among other benefits, makes it possible for the first time to ophthalmically deliver a therapeutically or prophylactically effective dose of an active agent having a low degree of solubility in water, such as linezolid, in a minimal number of doses.

In yet another embodiment, the present invention relates to a method of treating and/or preventing a disease or infection in an eye of a warm-blooded subject, the method comprising administering to the eye of the subject a therapeutically or prophylactically effective amount of one of the compositions of the invention described herein above.

The present invention also relates to a method of use of a composition of the present invention in manufacture of a medicament for topically treating or preventing a disease or infection of an eye of a warm-blooded subject.

The term "pharmaceutically acceptable" in relation to a cyclodextrin or other excipient herein means having no persistent detrimental effect on the eye or general health of the subject being treated. The pharmaceutical acceptability of a cyclodextrin depends, among other factors, on the particular cyclodextrin compound in question, on its concentration in the administered composition, and on the route of administration.

Except where the context demands otherwise, use of the singular herein will be understood to embrace the plural. For example, by indicating above that one embodiment of the composition of the invention comprises or "an oxazolidinone antibiotic drug" and "a pharmaceutically acceptable cyclodextrin compound", it will be understood that the composition can contain one or more such drugs and one or more such cyclodextrin compounds.

Prophylactic uses of a composition of the invention include prevention of disease or infection, including but not limited to, post-traumatic prophylaxis, especially post-surgical prophylaxis, and prophylaxis prior to ocular surgery.

What constitutes a "concentration effective for treatment and/or prevention of a disease or infection in an eye" depends, among other factors, on the particular active agent or agents being administered; the residence time provided by the particular formulation of the active agent; the species, age and body weight of the subject; the particular ophthalmic condition for which treatment or prophylaxis is sought; and the severity of the condition. In the case of linezolid, an effective concentration in a composition of the invention for topical administration to an eye will generally be found in the range from about 0.1 mg/ml to about 100 mg/ml, more typically about 0.5 mg/ml to about 80 mg/ml. For active agents, such as oxazolidinone compounds other than linezolid, an appropriate concentration range is one that is therapeutically equivalent to the linezolid concentration range indicated above.

The term "gum", as used herein, refers to any synthetic polymer, natural polysaccharide, or derivatized natural polysaccharide that is ophthalmically compatible and that increases the viscosity of a solution sufficiently to increase the viscosity of the solution in which it is found or to transform a drop of the solution into a semi-solid or gelatinous state after administration to an eye of a warm-blooded mammal. Examples of synthetic polymer gums include, but are not limited to, polyethylene glycol, polyvinyl pyrrolidone, carboxymethyl cellulose, polyvinyl alcohol and derivatives thereof, and Carbopol and derivatives thereof. Examples of natural polysaccharide gums include, but are not limited to, carrageenan, konjac, sodium alginate, aloe vera gel, agarose, guar, pectin, tragacanth, acacia, Arabic, curdlan, gellan, xanthan, scleroglucan, hyaluronic acid, or chitosan. Examples of derivatized natural polysaccharide gums include, but are not limited to, propyleneglycol alginate and hydroxypropyl guar.

The term "in situ gellable" herein is to be understood as embracing not only liquids of low viscosity that form gels upon contact with the eye or with lacrimal fluid in the exterior of the eye, but also more viscous liquids such as semi-fluid and thixotropic gels that exhibit increased or no significant loss of viscosity or gel stiffness upon administration to the eye.

The term "practical limit of solubility" in relation to a drug, such as the oxazolidinone of the present formulations, means the highest concentration at which the drug can be formulated in solution without risk of precipitation or crystallization of the drug during the normal range of manufacturing, packaging, storage, handling and use conditions. Typically, the practical limit of solubility is considerably lower than the true solubility limit in a given aqueous medium, for example about 70% of the true solubility limit. Thus, illustratively, for a drug having a true solubility limit in a given aqueous medium of 2.9 mg/ml, the practical limit of solubility is likely to be about 2 mg/ml.

The term "ophthalmically acceptable" with respect to a formulation, composition or ingredient herein means having no persistent detrimental effect on the treated eye or the functioning thereof, or on the general health of the subject being treated. It will be recognized that transient effects such as minor irritation or a "stinging" sensation are common with topical ophthalmic administration of drugs and the existence of such transient effects is not inconsistent with the formulation, composition or ingredient in question being "ophthalmically acceptable" as herein defined. However, preferred formulations, compositions and ingredients are those that cause no substantial detrimental effect, even of a transient nature.

The novel gel systems used in the compositions of the present invention provide viscosified or gel-forming systems with surprisingly good ocular tolerance, systemic safety, and compatibility with a variety of active agents. The variety of gel systems disclosed herein for use in the compositions of the invention also accord one the ability to obtain a wide range of viscous and viscoelastic or gelling behavior. More importantly, the compositions of the present invention are well tolerated in the eye, have good pseudo-plastic or yield stresses, and provide an enhanced residence time that allows for increased absorption of the active agent, relative to compositions of only a single species of gel. Appropriate novel gel systems of the present compositions can be tailored to create a variety of formulation and manufacturing choices.

These and other advantages of the compositions and methods of the present invention will become apparent from the following description of the invention and Examples, below.

DETAILED DESCRIPTION OF THE INVENTION

Figure 1A:
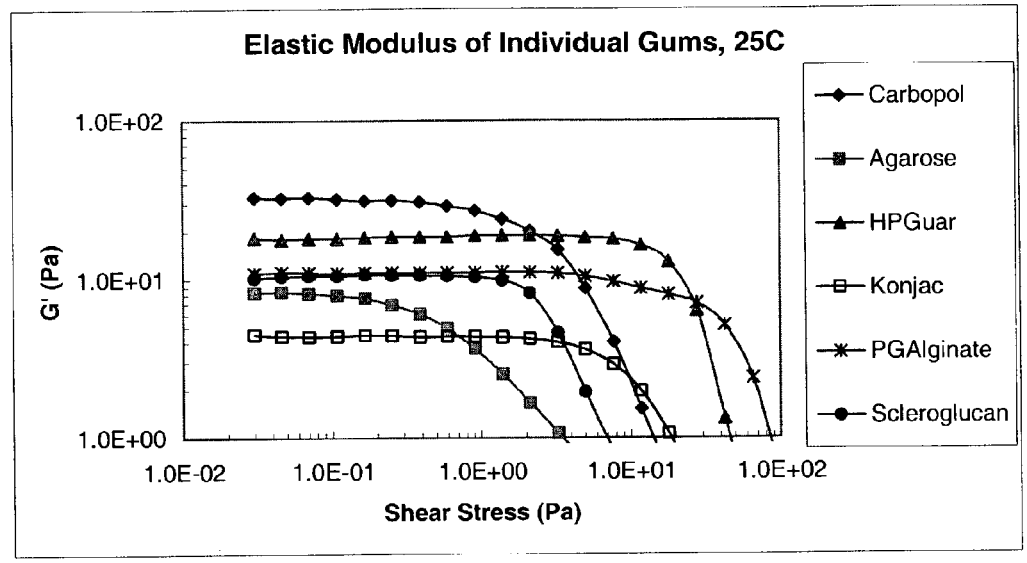
FIG. 1 is a set of three graphs illustrating the viseoelastic properties of individual gums in water at 25° C.: (a) elastic modulus vs. G', (b) viscous modulous G", and (c) phase angle, δ, each as a function of applied shear stress. The composition of the gum solutions tested are given in Table 1.

Although many different gums have been used in vehicles for the ophthalmic delivery of various drugs, few have been used in combination with one another. The combinations of gums of the present invention produce unexpected advantages over individual gums. The combination of gums used in any pharmaceutical composition of the present invention is preferably selected from the group consisting of konjac, scleroglucan, hydroxypropyl guar, propylene glycol alginate, sodium alginate, Carbopol and derivatives thereof (e.g., Carbopol 971), pectin, and agarose. New combinations of xanthan gum with gums listed above are also within the scope of the present invention.

Although, any of the gum combinations cited above can be used to produce viscous solutions that are suitable for ophthalmic dosing, specific combinations of gums can be selected to obtain specific viscosity or gelling characteristics. The nonionic gums (e.g., Konjac, HydroxyPropyl Guar, Agarose, Scleroglucan) do not show significant changes in rheological behavior when in contact with artificial tear fluid ("ATF"). The anionic gums (e.g., Carbopol, PropyleneGlycol Alginate) in contrast show a decrease in viscosity when mixed with ATF. Certain combinations of nonionic and anionic gums produce weakly gelling behavior or reduce the loss of viscosity. These combinations are not predictable. However, in general, an anionic gum is preferably combined with a neutral gum since the combination modulates the loss of viscosity of the two individuals. Due, at least in part, to the combination of gums, the composition of the present invention is preferably viscous or mucoadhesive, or even more preferably, both viscous or mucoadhesive.

Particularly preferred gum combinations used in the compositions of the present invention include a set of at least two ophthalmically compatible polymers selected from the group consisting of:

konjac and sodium alginate;
konjac and hydroxy propyl guar;
konjac and propylene glycol alginate;
konjac and Carbopol 971;
konjac and sodium alginate;
hydroxy propyl guar and agarose;
propylene glycol alginate and agarose;
propylene glycol alginate and scleroglucan;
propylene glycol alginate and agarose; and
scleroglucan and methyl cellulose.

Preferred gum combinations also include konjac and xanthan gum, xanthan gum and citrus pectin, and alginate and xanthan gum. Another preferred gum combination is konjac and carboxymethyl cellulose.

The gum combination in the composition of the present invention alone, or in combination with ophthalmically compatible excipients in the composition, preferably reduces the rate of removal of the composition from the eye by lacrimation, such that the composition has an effective residence time in the eye of about 2 to about 24 hours. Lacrimation is the production of tear fluid, and can remove matter from the eyes both by external wash-out and by lacrimal drainage into the nasopharyngeal cavity via the nasolacrimal ducts. A consequence of removal of an ophthalmic composition from a treated eye is a reduced concentration of the active agent in the lacrimal fluid and hence in the target tissue.

For sustained contact of the composition with the eye, and corresponding increased delivery of the active agent component of the composition to the eye, the concentration in the lacrimal fluid and in the target tissue, e.g., the conjunctiva or the cornea, preferably remains above the $MIC_{90}$ for the active agent in question. When the active agent is an antibiotic drug, such as an oxazolidinone, the $MIC_{90}$ is the minimum inhibitory concentration for 90% of the target organisms, such as infective gram-positive bacteria. When the active agent is linezolid, the $MIC_{90}$ is about 4 μg/ml. By "effective residence time" herein is meant a period of time following application of the composition to the eye during which the concentration of the active agent in the lacrimal fluid and/or in the target tissue remains above the $MIC_{90}$ for that active agent.

Preferably no more than 3 drops, more preferably no more than 2 drops, and most preferably no more than 1 drop, each of about 5 μl to about 50 μl, preferably about 15 to about 30 μl, for example about 25 μl, should contain the desired dose of the active agent for administration to an eye. Administration of a larger volume to the eye risks loss of a significant portion of the applied composition by lacrimal drainage.

In a preferred embodiment, the composition is an in situ gellable aqueous composition, more preferably an in situ gellable aqueous solution. Such a composition comprises a gelling agent in a concentration effective to promote gelling upon contact with the eye or with lacrimal fluid in the exterior of the eye. Indeed, it can be advantageous to formulate a composition of the invention as a gel, to minimize loss of the composition immediately upon administration, as a result for example of lacrimation caused by reflex blinking. Although it is preferred that such a composition exhibit further increase in viscosity or gel stiffness upon administration, this is not absolutely required if the initial gel is sufficiently resistant to dissipation by lacrimal drainage to provide the effective residence time specified herein.

In a preferred embodiment, the composition of the present invention as described above is used for amelioration of dry eye symptoms. When the composition is to be used for the amelioration of dry eye symptoms, it preferably further includes at least one additional component selected from the group consisting of polyvinyl alcohol, methyl cellulose, hydroxypropyl cellulose. The composition preferably further includes at least one agent that improves ocular tolerance, such as aloe vera gel, a buffering agent, and a tonicity modifier. The composition optionally includes an antimicrobial agent and/or a preservative.

In addition to the combination of gums described above, the pharmaceutical composition of the present invention comprises a pharmaceutically effective amount of an active agent. The active agent is any drug useful in treating or preventing any disease or infection of the eye of a warm-blooded animal. Any drug having utility as a topical ophthalmic application can be used as an active agent in the composition of the invention. Such drugs include without limitation antimicrobials; demulcents; antimycotics, antivirals and other anti-infectives; steroids, NSAIDs, selective cyclooxygenase-2 inhibitors, cyclooxygenase-1 inhibitors and other anti-inflammatory agents; acetylcholine blocking agents; adrenergic agonists, beta-adrenergic blocking agents and other antiglaucoma agents; antihypertensives; antihistamines; anticataract agents; and topical and regional anesthetics. Illustrative specific drugs include acebutolol, aceclidine, acetylsalicylic acid (aspirin), $N^4$ acetylsulfisoxazole, alclofenac, alprenolol, amfenac, amiloride, aminocaproic acid, p-aminoclonidine, aminozolamide, anisindione, apafant, atenolol, bacitracin, benoxaprofen, benoxinate, benzofenac, bepafant, betamethasone, betaxolol, bethanechol, bimatprost, brimonidine, bromfenac, bromhexine, bucloxic acid, bupivacaine, butibufen, carbachol, carprofen, celecoxib, cephalexin, chloramphenicol, chlordiazepoxide, chlorprocaine, chlorpropamide, chlortetracycline, cicloprofen, cinmetacin, ciprofloxacin, clidanac, clindamycin, clonidine, clonixin, clopirac, cocaine, cromolyn, cyclopentolate, cyproheptadine, demecarium, deracoxib, dexamethasone, dibucaine, diclofenac, diflusinal, dipivefrin, dorzolamide, enoxacin, epinephrine, erythromycin, eserine, estradiol, ethacrynic acid, etidocaine, etodolac, fenbufen, fenclofenac, fenclorac, fenoprofen, fentiazac, flufenamic acid, flufenisal, flunoxaprofen, fluorocinolone, fluorometholone, flurbiprofen and esters thereof, fluticasone propionate, furaprofen, furobufen, furofenac, furosemide, gancyclovir, gentamicin, gramicidin, hexylcaine, homatropine, hydrocortisone, ibufenac, ibuprofen and esters thereof, idoxuridine, indomethacin, indoprofen, interferons, isobutylmethylxanthine, isofluorophate, isoproterenol, isoxepac, ketoprofen, ketorolac, labetolol, lactorolac, latanoprost, levo-bunolol, lidocaine, linezolid, lonazolac, loteprednol, meclofenamate, medrysone, mefenamic acid, mepivacaine, metaproterenol, methanamine, methylprednisolone, metiazinic, metoprolol, metronidazole, minopafant, miroprofen, MK-663, modipafant, nabumetome, nadolol, namoxyrate, naphazoline, naproxen and esters thereof, neomycin, nepafenac, nitroglycerin, norepinephrine, norfloxacin, nupafant, olfloxacin, olopatadine, oxaprozin, oxepinac, oxyphenbutazone, oxyprenolol, oxytetracycline, parecoxib, penicillins, perfloxacin, phenacetin, phenazopyridine, pheniramine, phenylbutazone, phenylephrine, phenylpropanolamine, phospholine, pilocarpine, pindolol, pirazolac, piroxicam, pirprofen, polymyxin, polymyxin B, prednisolone, prilocaine, probenecid, procaine, proparacaine, protizinic acid, rimexolone, rofecoxib, salbutamol, scopolamine, sotalol, sulfacetamide, sulfanilic acid, sulindac, suprofen, tenoxicam, terbutaline, tetracaine, tetracycline, theophyllamine, timolol, tobramycin, tolmetin, travoprost, triamcinolone, trimethoprim, trospectomycin, valdecoxib, vancomycin, vidarabine, vitamin A, warfarin, zomepirac and pharmaceutically acceptable salts thereof.

The active agent is more preferably a steroid or an NSAID, such as dexamethasone or diclofenac, a COX-2 inhibitor, such as celecoxib or valdecoxib, or an antibiotic, such as an oxazolidinone antibiotic drug, for example, linezolid.

When the antibiotic drug is an oxazolidinone antibiotic drug, i.e., one having an oxazolidinone moiety as part of its chemical structure, it is preferably a compound of formula (I)

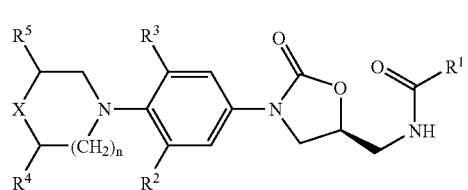

(I)

wherein:

$R^1$ is selected from (a) H, (b) $C_{1-8}$ alkyl optionally substituted with one or more F, Cl, OH, $C_{1-8}$ alkoxy, $C_{1-8}$ acyloxy or benzoxy groups, and including $C_{3-6}$ cycloalkyl, (c) amino, (d) mono- and di($C_{1-8}$ alkyl) amino and (e) $C_{1-8}$ alkoxy groups;

$R^2$ and $R^3$ are independently selected from H, F and Cl groups;

$R^4$ is H or $CH_3$;

$R^5$ is selected from H, $CH_3$, CN, $CO_2R^1$ and $(CH_2)_mR^6$ groups, where $R^1$ is as defined above, $R^6$ is selected from H, OH, $OR^1$, $OCOR^1$, $NHCOR^1$, amino, mono- and di($C_{1-8}$ alkyl)amino groups and m is 1 or 2;

n is 0, 1 or 2; and

X is O, S, SO, $SO_2$, $SNR^7$ or $S(O)NR^7$ where $R^7$ is selected from H, $C_{1-4}$ alkyl (optionally substituted with one or more F, Cl, OH, $C_{1-8}$ alkoxy, amino, $C_{1-8}$ mono- or di($C_{1-8}$ alkyl)amino groups), and p-toluenesulfonyl groups;

or a pharmaceutically acceptable salt thereof.

Particularly preferred oxazolidinone drugs according to this embodiment are compounds of formula (II) wherein $R^1$ is $CH_3$; $R^2$ and $R^3$ are independently selected from H and F but at least one of $R^2$ and $R^3$ is F; $R^4$ and $R^5$ are each H; n is 1; and X is O, S or $SO_2$. In another preferred embodiment, the oxazolidinone drug is selected from linezolid, eperezolid, N-((5S)-3-(3-fluoro-4-(4-(2-fluoroethyl)-3-oxopiperazin-1-yl)phenyl)-2-oxooxazolidin-5-ylmethyl)acetamide, (S)—N-[[3-[5-(3-pyridyl)thiophen-2-yl]-2-oxo-5-oxazolidinyl]methyl]acetamide, (S)—N-[[3-[5-(4-pyridyl)pyrid-2-yl]-2-oxo-5-oxazolidinyl]methyl]acetamide hydrochloride and N-[[(5S)-3-[4-(1,1-dioxido-4-thiomorpholinyl)-3,5-difluorophenyl]-2-oxo-5-oxazolidinyl]methyl]acetamide.

According to either of these preferred embodiments, an especially preferred oxazolidinone drug is linezolid. Another especially preferred oxazolidinone drug is N-[[(5S)-3-[4-(1,1-dioxido-4-thiomorpholinyl)-3,5-difluorophenyl]-2-oxo-5-oxazolidinyl]methyl]acetamide. The invention is illustrated herein with particular reference to linezolid, and it will be understood that any other oxazolidinone antibiotic compound can, if desired, be substituted in whole or in part for linezolid, with appropriate adjustment in concentration and dosage ranges, in the compositions and methods herein described.

Oxazolidinone compounds used in compositions of the invention can be prepared by a process known per se, in the case of linezolid and eperezolid, for example, by processes described in the following patents, each of which is individually incorporated herein by reference.

U.S. Pat. No. 5,688,791.

U.S. Pat. No. 5,837,870.

International Patent Publication No. WO 99/24393.

Other oxazolidinone drugs can be prepared by processes known per se, including processes set forth in patent publications disclosing such drugs.

The oxazolidinone embodiment of the compositions of the present invention is illustrated herein with particular reference to linezolid. However, it is understood that any other oxazolidinone antimicrobial drug can, if desired, be substituted in whole or in part for linezolid, with appropriate adjustment in concentration and dosage ranges, in the compositions and methods herein described.

Linezolid is usefully present in a composition of the invention at a concentration of about 3 mg/ml to as high a concentration as is practically enabled by the cyclodextrin present therewith, for example about 100 mg/ml. Preferably in a composition intended for direct administration as formulated, the concentration of linezolid is about 0.1 mg/ml to about 100 mg/ml, more preferably about 0.5 to about 80 mg/ml, for example about 50 mg/ml. Useful concentrations of other oxazolidinone drugs are those that are therapeutically equivalent to the linezolid concentration ranges given immediately above.

When an active agent having low solubility in water is used in a composition of the present invention, the active agent is preferably either present at a concentration where it is soluble or it is present at a higher concentration but an ophthalmically compatible solubilizing agent is included to ensure the active agent is in solution. Active agents having low solubility in water suitably formulated in this embodiment of the compositions of the present invention include, but are not limited to dextramethasone, diclofenac, valdecoxib, celecoxib, and low solubility antibiotic drugs, including oxazolidinone antibiotic drugs, such as linezolid. Such low solubility active agents are preferably present in a higher concentration in the composition of the present invention, facilitated by the presence of a solubilizing agent therein.

In some embodiments of the present invention, the compositions fur comprise a solubilizing agent. Solubilizing agents suitable for use in the compositions of the invention include nonionic surfactants such as Polysorbate 80 or tyloxapol, or cosolvents such as propylene glycol, polyethylene glycol, or triacetin. The solubilizing agent is preferably a cyclodextrin derivative.

Derivatives of cyclodextrin, including α-, β, and γ-cyclodextrins and derivatives thereof, such as ether and mixed ether derivatives, and derivatives bearing sugar residues have been disclosed as being suitable for use in the solubilization of various drugs that are only sparingly soluble in water. EP 0149 197 B2 (Canadian counterpart, CA 1222697), incorporated by reference herein, discloses the suitability of partially etherified β-cyclodextrin and derivatives thereof, including hydroxyethyl, hydroxypropyl, and hydroxypropyl-methyl-β cyclodextrin for the solubilization of various types of drugs which are instable or only sparingly soluble in water.

U.S. Pat. No. 4,727,064, incorporated by reference herein, discloses the use of hydroxypropyl-β-cyclodextrin and the use of mixtures of that cyclodextrin derivative, diethylaminoethyl-β-cyclodextrin, carboxymethyl-β-cyclodextrin, and carboxamidomethyl-β-cyclodextrin to assist in the dissolution of drugs, but does not disclose the solibilization of any oxazolidinone using such a solubility enhancer.

The cyclodextrin compound with which an active agent is formulated in this embodiment of the present invention is preferably selected from α-cyclodextrin, β-cyclodextrin, γ-cyclodextrin, alkylcyclodextrins (e.g., methyl-β-cyclodextrin, dimethyl-β-cyclodextrin, diethyl-β-cyclodextrin), hydroxyalkylcyclodextrins (e.g., hydroxyethyl-β-cyclodextrin, hydroxypropyl-β-cyclodextrin), carboxyalkylcyclodextrins (e.g., carboxymethyl-β-cyclodextrin) and sulfoalkylether cyclodextrins (e.g., sulfobutylether-β-cyclodextrin). More preferred are hydroxyalkyl-β-cyclodextrins and sulfoalkylether-β-cyclodextrins; still more preferred are hydroxypropyl-β-cyclodextrin and sulfobutylether-β-cyclodextrin.

If desired, complexation of the active agent by the cyclodextrin compound can be increased by addition of a water-soluble polymer such as carboxymethylcellulose or a salt thereof, hydroxypropylmethylcellulose or polyvinylpyrrolidone, as described by Loftsson (1998), *Pharmazie,* 53, 733–740.

When included, the cyclodextrin is preferably present at a concentration effective to enhance the solubility of the active agent. In practice and in view of the high cost of cyclodextrins, the amount of the cyclodextrin present in a composition of the invention is preferably only slightly greater, for example no more than about 50% greater, than a minimum amount required to maintain the active agent in solution at the desired concentration. The cyclodextrin is preferably present in an amount above the practical limit of solubility of the active agent.

Where the composition is intended for direct administration to an eye as formulated, suitable concentrations of cyclodextrin will be found in a range from about 1 mg/ml to about 500 mg/ml, more commonly about 5 mg/ml to about 300 mg/ml, and most commonly about 5 to about 250 mg/ml.

The composition is preferably in the form of an aqueous solution, more preferably, one that can be presented in the form of eye drops. By means of a suitable dispenser, a desired dosage of the active agent can be metered by administration of a known number of drops into the eye. For example, for a drop volume of 25 µl, administration of 1–6 drops will deliver 25–150 µl of the composition. Suitable dispensers are illustratively disclosed in International Patent Publication No. WO 96/06581, incorporated herein by reference.

If necessary, an appropriate amount of a calcium complexing agent such as ethylene diamine tetraacetic acid (EDTA) or a salt, for example the disodium salt, thereof, can be included in a composition of this particular embodiment to complex excess calcium ions and prevent gel formation during storage. EDTA or a salt thereof can suitably be included in an amount of about 0.01% to about 0.5%. Especially where a preservative is present, it is especially preferred to include EDTA or a salt thereof, more particularly disodium EDTA, in an amount of about 0.025% to about 0.1%, by weight, as synergistically enhanced antimicrobial activity can result.

A composition of the invention can optionally contain an antimicrobially effective amount of a preservative, provided that the preservative does not substantially inhibit the effectiveness of the active agent or of any solubilizing agent in the composition. Illustratively, the composition can contain a preservative selected from the group consisting of imidazolidinyl urea in an amount of about 0.03% to about 0.5%; methylparaben in an amount of about 0.015% to about 0.25%; propylparaben in an amount of about 0.005% to about 0.01%; phenoxyethanol in an amount of about 0.25% to about 1%; disodium EDTA in an amount of about 0.05% to about 0.2%; thimerosal in an amount of 0.001% to about 0.15%; chlorobutanol in an amount of about 0.1% to about 0.5%; sorbic acid in an amount of about 0.05% to about 0.2%; benzalkonium chloride in an amount of about 0.001% to about 0.02%; any suitable combination of any of the above. Any of the above-cited preservatives can also be combined with other suitable preservatives and included in the compositions of the present invention. All amount figures above are provided as a percent by weight of the total composition.

The composition of the invention preferably further comprises an ophthalmically compatible antioxidant. Preferred antioxidants include, but are not limited to: sodium bisulfite, sodium metabisulfite, sodium thiosulfate, acetyl cysteine, cysteine, thioglycerol, sodium sulfite, acetone sodium bisulfite, dithioerythreitol, dithiothreitol, thiourea, propyl gallate, methionine, and erythorbic acid.

A composition of the present invention can optionally further comprise glycerin in an amount of about 0.1% to about 5%, more preferably about 1% to about 2.5%, for example about 1.5% to about 2%, by weight. Glycerin can also be useful to increase viscosity of the composition and for adjustment of osmolality.

The composition optionally further includes at least one ophthalmically acceptable salt in an amount required to bring osmolality of the composition into an ophthalmically acceptable range. In some cases, the salts can also be antioxidants, such as those cited herein, above. Salts suitable for use in adjusting osmolality include those having sodium, potassium or ammonium cations and chloride, citrate, ascorbate, borate, phosphate, bicarbonate, sulfate, thiosulfate or bisulfite anions; preferred salts include sodium chloride, potassium chloride, sodium thiosulfate, sodium bisulfite and ammonium sulfate, with sodium chloride being especially preferred. Other solutes suitable for adjustment of osmolality include sugars, for example dextrose, manitol, xylitol, and sucrose.

The composition of the invention optionally further includes at least one ophthalmically acceptable pH adjusting agent and/or buffer, including an acid such as acetic, boric, citric, lactic, phosphoric and hydrochloric acids; a base such as sodium hydroxide, sodium phosphate, sodium borate, sodium citrate, sodium acetate, sodium lactate and tris-hydroxymethylaminomethane; and a buffer such as citrate/dextrose, sodium bicarbonate and ammonium chloride. Such an acid, base and/or buffer is preferably included in an amount required to maintain pH of the composition in an ophthalmically acceptable range.

Accordingly, a particular embodiment of the invention is a composition as described hereinabove, further comprising a buffering agent and/or an agent for adjusting osmolality in amounts whereby the solution is substantially isotonic and has a physiologically acceptable pH.

Optionally, an ophthalmically acceptable xanthine derivative such as caffeine, theobromine or theophylline can be included in the composition, substantially as disclosed in U.S. Pat. No. 4,559,343 to Han & Roehrs, incorporated herein by reference. Inclusion of the xanthine derivative can reduce ocular discomfort associated with administration of the composition.

Optionally, the composition further comprises at least one ophthalmically acceptable surfactant, a preferably nonionic surfactant, to enhance physical stability or for other purposes. Suitable nonionic surfactants include polyoxyethylene fatty acid glycerides and vegetable oils, e.g., polyoxyethylene (60) hydrogenated castor oil; and polyoxyethylene alkylethers and alkylphenyl ethers, e.g., octoxynol 10, octoxynol 40.

The composition of the invention optionally further comprises an ophthalmically acceptable mucoadhesive polymer. The mucoadhesive polymer is preferably selected from hydroxypropylmethylcellulose, carboxymethylcellulose, carbomer (acrylic acid polymer), poly(methylmethacrylate), polyacrylamide, polycarbophil, polyethylene oxide, acrylic acid/butyl acrylate copolymer, sodium alginate and dextran.

Optionally, one or more antioxidants can be included in the composition to enhance chemical stability where required. Suitable antioxidants include ascorbic acid, sodium metabisulfite, sodium thiosulfate, and thioglycerol.

In another embodiment, the composition is either used in co-therapy, co-administration, or coformulated with at least one other active agent. The second active agent preferably cooperates with the first active agent in the composition in treating and/or preventing the same disease, infection, or other condition of the eye treated or prevented by the initial active agent. Alternatively, the second active agent is used to treat a related or unrelated condition simultaneously affecting the eye. When the first active agent is an antibiotic drug, such as an oxazolidinone antibiotic drug, that is effective against gram-positive bacteria, the composition can be used in co-therapy, co-administration, or co-formulated with at least one additional active agent that is effective against gram-negative bacteria. The first and/or second active agent can also be a drug other than an antibiotic, such as an anti-inflammatory agent, such as a selective COX-2 inhibitor.

When an active agent effective against gram-negative bacteria is selected for co-therapy, co-administration, or co-formulation, it can illustratively be selected from aminoglycosides, cephalosporins, diaminopyridines, fluroquinolones, sulfonamides and tetracyclines. Among particular antimicrobial drugs of these and other classes, each of the following may illustratively be useful as the second antimicrobial drug according to an embodiment of the present invention: amikacin, cefixime, cefoperazone, cefotaxime, ceftazidime, ceftizoxime, ceftriaxone, chloramphenicol, ciprofloxacin, clindamycin, colistin, domeclocycline, doxycycline, gentamicin, mafenide, methacycline, minocycline, neomycin, norfloxacin, ofloxacin, oxytetracycline, polymyxin B, pyrimethamine, silver sulfadiazine, sulfacetamide, sulfisoxazole, tetracycline, tobramycin and trimethoprim.

Compositions of the present invention can be prepared by processes known in the art, including by simple admixture, with agitation as appropriate, of the ingredients. When a cyclodextrin compound is included in the composition, an aqueous solution of the cyclodextrin compound is preferably prepared first, and the active agent, preferably in finely divided solid particulate form, is added to that solution with agitation until it is fully dissolved. Where it is desired to prepare a buffered isotonic solution buffering agents and agents for adjustment of osmolality can be added at any stage but are preferably present in solution with the cyclodextrin compound before addition of the active agent. Similarly, where it is desired to include any of the other additional alternative components cited above in the composition they can be added at any stage, but, are preferably present in the solution when the cyclodextrin compound before addition of the active agent. Processes for preparing an ophthalmic composition of the invention are preferably conducted so as to provide a sterile product.

In another preferred embodiment, the combination of gums of the present invention can be used to deliver aqueous suspensions of active agents and improve their efficacy in the eye.

In a method of the invention for treating or preventing infective disease, an ophthalmic composition as described above in a therapeutically or prophylactically effective dose is administered to at least one eye of a subject in need thereof. The subject is preferably a warm-blooded animal, more preferably selected from dogs, cats, horses, cattle, sheep and pigs. However, the subject is more preferably a human being.

As indicated above, certain embodiments of the method of the invention are particularly useful where the infective disease arises through infection by one or more gram-positive bacteria. Where broader-spectrum antibiotic activity, extending to gram-negative bacteria, is required, a second antimicrobial drug can be administered in co-therapy, including for example coformulation, with the present composition. The second antimicrobial drug is selected to be effective against target gram-negative bacteria. Such co-therapy and coformulation are embodiments of the present invention.

An appropriate dosage, frequency and duration of administration, i.e., treatment regimen, to be used in any particular situation will be readily determined by one of skill in the art without undue experimentation, and will depend, among other factors, on the particular active agent(s) present in the composition, on the particular ophthalmic condition being treated or prevented, on the age, weight and general physical condition of the subject, and on other medication being administered to the subject. It is preferred that response of the ophthalmic condition to treatment according to the present method be monitored and the treatment regimen be adjusted if necessary in light of such monitoring.

Frequency of administration is typically such that the dosing interval, i.e., the period of time between one dose and the next, during waking hours is about 2 to about 12 hours, more typically about 3 to about 8 hours, for example about 4 to about 6 hours. It will be understood by those of skill in the art that an appropriate dosing interval is dependent to some degree on the length of time for which the selected composition is capable of maintaining a concentration of the active agent, such as an oxazolidinone antibiotic, in the lacrimal fluid and/or in the target tissue (e.g., the conjunctiva) above the $MIC_{90}$. Ideally the concentration remains above the $MIC_{90}$ for at least 100% of the dosing interval. Where this is not achievable it is desired that the concentration should remain above the $MIC_{90}$ for at least about 60% of the dosing interval, in a worst case at least about 40% of the dosing interval.

The following examples are illustrative of the process and products of the present invention. They are not to be construed as limiting. All experiments were or are done at room temperature and pressure, unless otherwise indicated.

EXAMPLES

The following Examples illustrate aspects of the present invention but are not to be construed as limitations.

Example 1

Rheological Assays

The following Theological characterization assays were used to characterize the compositions prepared as described in Examples 4 to 8, below. Gum solutions were studied "As Is" at 25° C. to characterize the vehicle or formulation itself. The same solutions were also diluted in a 3:1 ratio with Artificial Tear Fluid ("ATF"), allowed to sit for 30 minutes, and then analyzed on the Rheometer at 35° C., to mimic conditions in the eye. The Artificial Tear Fluid used in this Example had the following composition: 6.8 g. NaCl, 2.25 gm $NaHCO_3$, 1.41 gm KCl, and 0.085 g. $CaCl_2.2H_2O$. Both the As Is and the ATF samples were assayed under the following conditions.

Both of the above sets of samples were tested by taking oscillatory rheology measurements on a Bohlin CVO50 Controlled Stress Instrument using a cone and plate CP 4°/40 mm measurement system, set to perform a stress-sweep using parameters designed to examine the range of linear viscoelastic behavior of the gels. Parameter settings used:

Pre-Shear: Off
Sample rest time after application: 5 minutes
Sweep type: Amplitude
Range: Log
Start Stress: 0.03 Pa
End Stress: 100 Pa
No. of Points: 20
Frequency: 1 Hz
Ramp direction: Up/Down The method examined the viscoelasticity of the test sample, reported in terms of it elastic modulus G', the viscous modulus G", and its phase angle δ, as a function of oscillatory shear stress placed upon the gel. A gel can be characterized by these three parameters. G' indicates the elasticity of the gel to this shear, i.e., its resilience to deformation before it yields. Thus an elastic gel will be able to absorb the applied energy for a greater range of shear stresses before it breaks down. This is indicated by a nearly horizontal line on the G' plot. The break down of gel structure is indicated by the point at which G' drops. The shear stress at which this happens is the critical shear stress, and the higher the number, the more resilient and stiffer the gel. Similarly, the G" is a measure of the viscous nature of the gel, i.e., how much it will flow as a consequence of the applied shear. Some gels are stiff and resist flow until they break down. Others flow at all shears. High G' and Low G" implies a stiff thick gel, while low G' and high G" implies a runny gel.

The ratio between G' and G" is δ, and gives a measure of the relative "solid" to "fluid" nature of the gel. Phase angles near zero imply a nearly solid-like behavior while those near 90° imply a liquid-like behavior.

Example 2

In Vivo PK Adsorption Tests

Formulations prepared with 10 mg/mL linezolid as described in Examples below were administered to rabbit eyes to assess the concentration of Linezolid in the conjunctiva, 1 hour after application. To each 1 mL of the formulation, 0.5 mg of $^{14}C$-labeled Linezolid was added.

Four healthy male New Zealand white rabbits of body weight 1.8 to 2.5 kg were assigned to treatment with the formulation. To each of the eyes of the rabbit, 25 μL of the test formulation was applied using a pipette. Rabbits were sacrificed 1 hour after application, and eye tissues were excised. Excised tissues were combusted for liquid scintillation counting to determine radioactivity as a measure of amount of radioactivity present. Radioactive counts were converted by calculation to concentration of linezolid in μg/g.

Results of this assay are reported in Example 9, below.

Example 3

In Vivo Ocular Irritation Test

Healthy male New Zealand white rabbits of body weight 1.8 to 2.5 kg were dosed with approximately 25 μL of the same test formulation used in Example 2 every two hours, and visually assessed for irritation during the dosing episode and the state of the eye monitored post-dosing.

Results of this assay are reported in Example 9, below.

Example 4

Formulations with Individual Gums

Figure 1B:
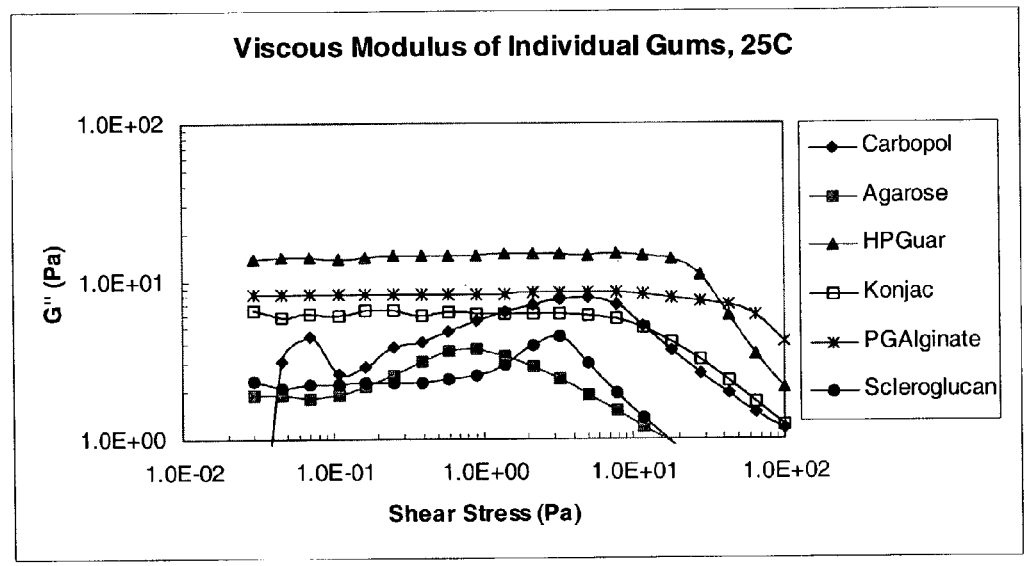
Figure 1C:
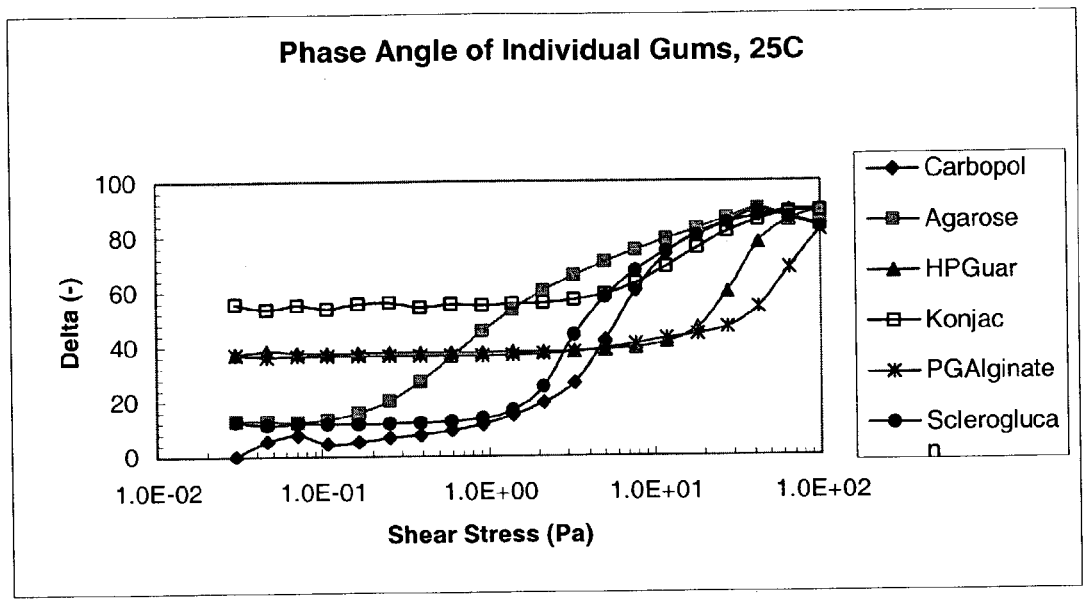
Figure 2A:
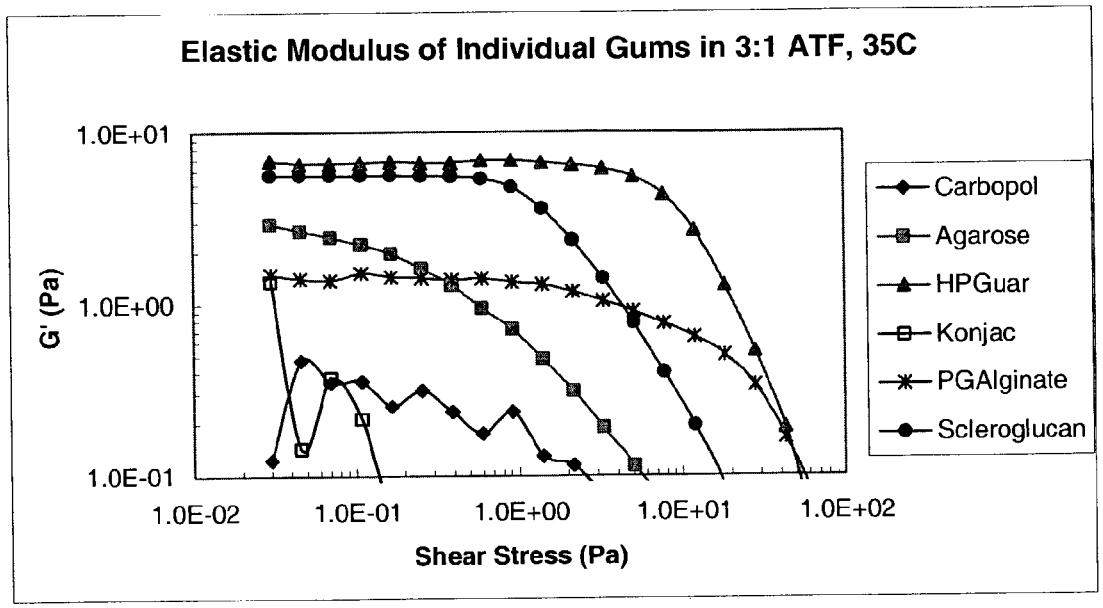
FIG. 2 is a set of three graphs illustrating the viseoelastic properties of individual gums in water mixed with ATF in a ratio of 3:1 at 35° C.: (a) elastic modulus, G', (b) viscous modulous, G", and (c) phase angle, δ, each as a function of applied shear stress. The composition of the gum solutions are given in Table 1.
Figure 2B:
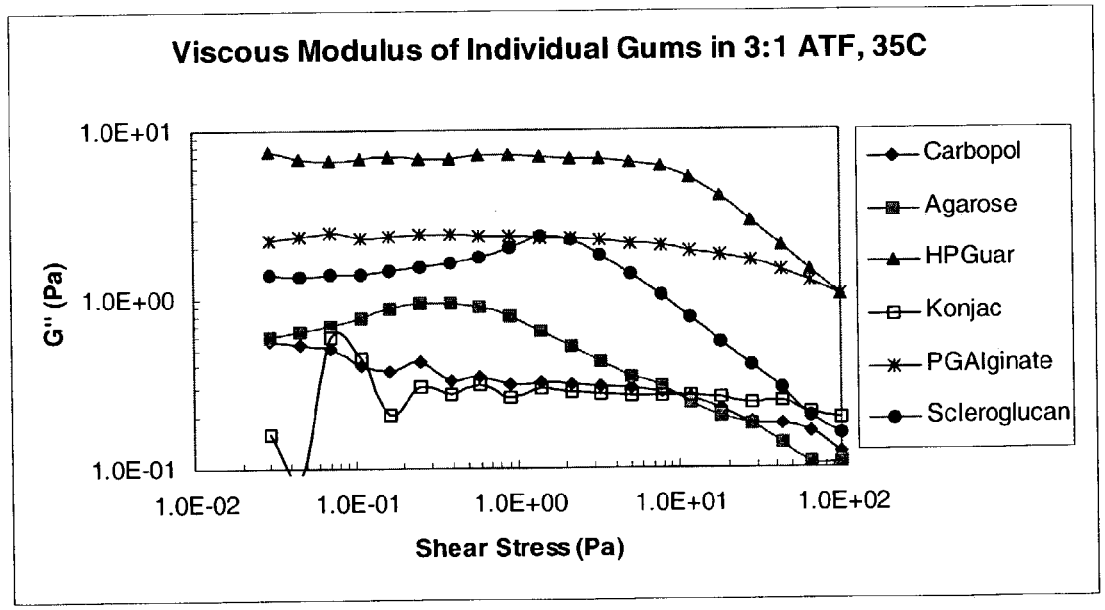
Figure 2C:
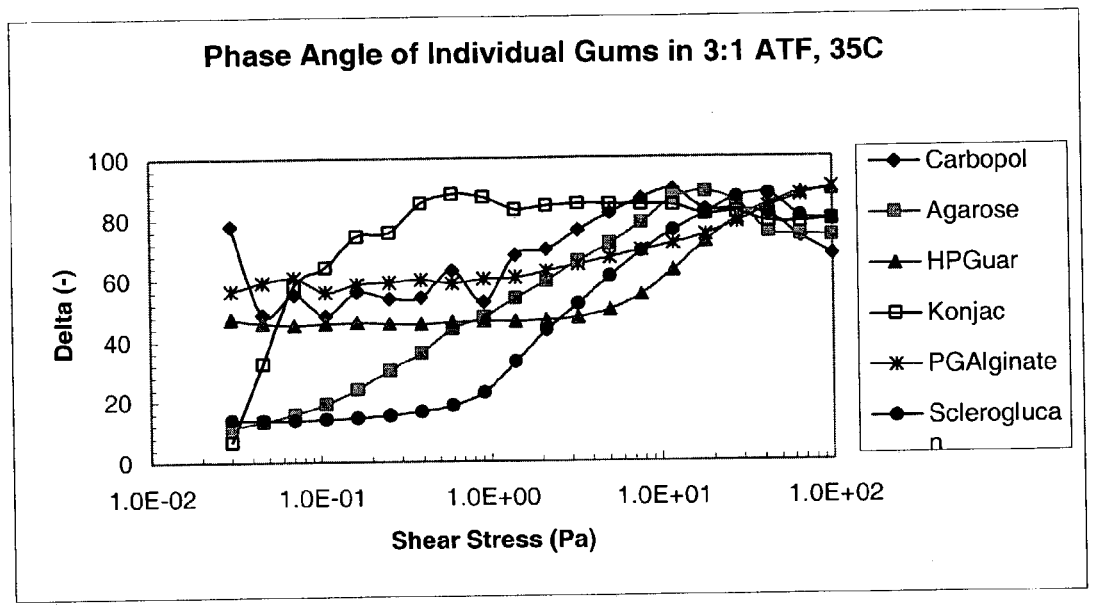

Various vehicles containing only a single gum species were made as described in Table 1, below. The viscoelastic behavior was examined at 25° C. and with 3:1 ATF at 35° C., as described in Example 1. While all vehicles formed good viscoelastic solutions at 25° C., the Carbopol and konjac vehicles lost a significant portion of their elasticity, and become predominantly viscous solutions (FIGS. 1a–c, 2a–c) in the ATF test.

Comments in Tables 1–5 were the result of qualitative assessments based on examination of the above mentioned data as well visual observations made of the compositions.

TABLE 1

Summary of rheological and visual characterization of vehicles composed of individual gums in water.

| ID | Composition | Behavior at 25° C. | Behavior with 3:1 ATF at 35° C. |
|---|---|---|---|
| 1 | 0.8% Carbopol 971P | Thick elastic gel | Weak viscous fluid |
| 2 | 0.15% Agarose VII | Thick viscoelastic fluid | Thick viscoelastic fluid |
| 3 | 1% HydroxyPropyl Guar | Thick elastic gel | Thick elastic gel |
| 4 | 0.4% Konjac | Thick viscoelastic fluid | Weak viscous fluid |
| 5 | 1.5% PropyleneGlycol Alginate | Thick viscoelastic fluid | Viscoelastic fluid |
| 6 | 0.6% Scelroglucan | Thick elastic gel | Viscoelastic gel |
| 7 | 2% Base-Hydrolyzed Citrus Pectin | Thick fluid | Weak elastic gel formation |
| 8 | 1.5% Sodium Alginate (high guluronic acid content) | Thick fluid | Weak elastic gel formation |

| ID | Composition | Formulation feasibility |
|---|---|---|
| 1 | 0.8% Carbopol 971P | Too thick to manufacture or instill as is. Looses gel nature on contact with ions. Use pH effect to formulate. |
| 2 | 0.15% Agarose VII | Possible to use as a viscous drop |
| 3 | 1% HydroxyPropyl Guar | Too thick to manufacture or instill as is |
| 4 | 0.4% Konjac | Possible to use as a viscous drop but collapses on contact with ions |
| 5 | 1.5% PropyleneGlycol Alginate | Possible to use as a viscous drop |
| 6 | 0.6% Scelroglucan | Too thick to manufacture or instill as is |
| 7 | 2% Base-Hydrolyzed Citrus Pectin | Possible to use as a viscous drop |
| 8 | 1.5% Sodium Alginate (high guluronic acid) | Possible to use as a viscous drop |

In certain cases (ID#s 1, 3, and 6, corresponding to the Carbopol, HydroxyPropyl Gaur, and Scleroglucan samples, respectively) the vehicle was found to be very viscous, presenting manufacturing difficulties and also making the dispensation of a dose by a simple dropper bottle difficult.

The agarose vehicle (ID# 2) remained a viscous liquid if used at the 0.15% level. However the intrinsic gelation behavior is such that at 0.25% it forms a stiff gel at room temperature and becomes unusable. Similarly, the konjac vehicle (ID# 4) offered good initial viscosity. However, the vehicle displayed no gelation ability.

It was discovered that the properties of the various vehicles described above could be altered and optimized by combining the gums in various proportions, as is illustrated in the remaining Examples, below.

Example 5

Combination of Gums with Konjac

Figure 3A:
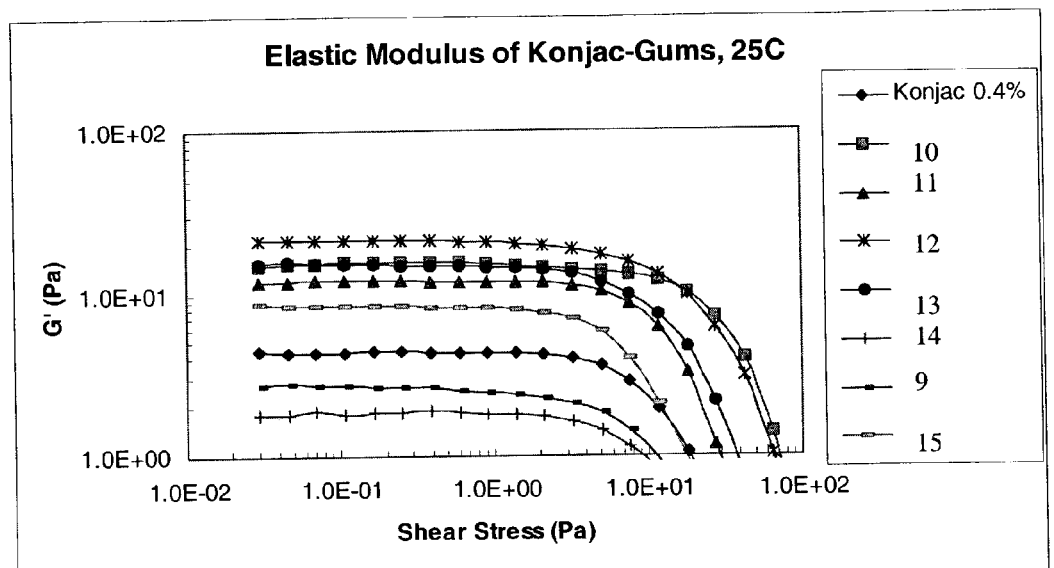
FIG. 3 is a set of three graphs illustrating the viseoelastic properties of Konjac combined with a variety of other gums in water at 25° C.: (a) elastic modulus, G', (b) viscous modulous, G", and (c) phase angle, δ, each as a function of applied shear stress. The composition of the gum solutions tested are given in Table 2.
Figure 3B:
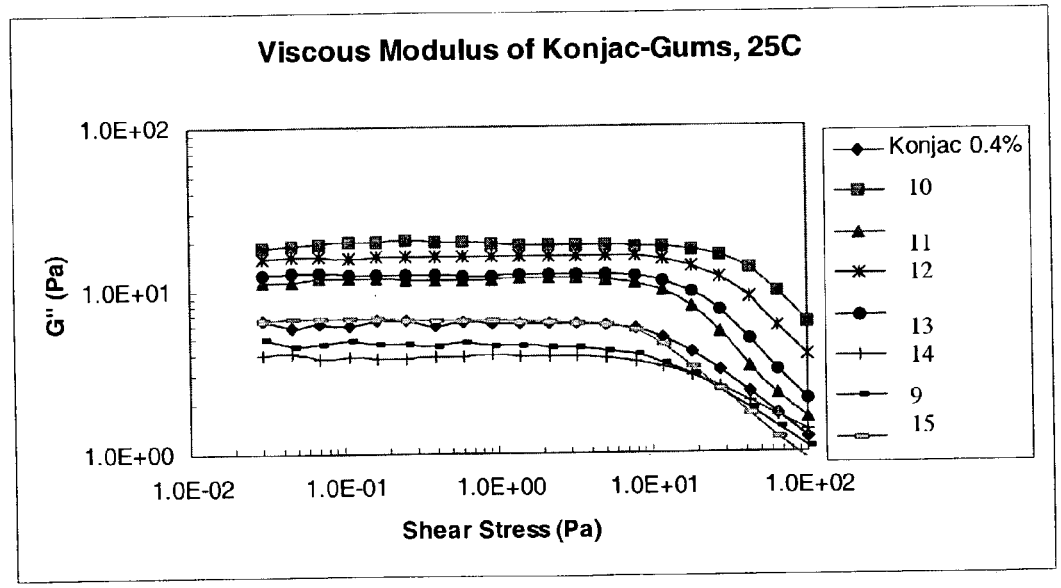
Figure 3C:
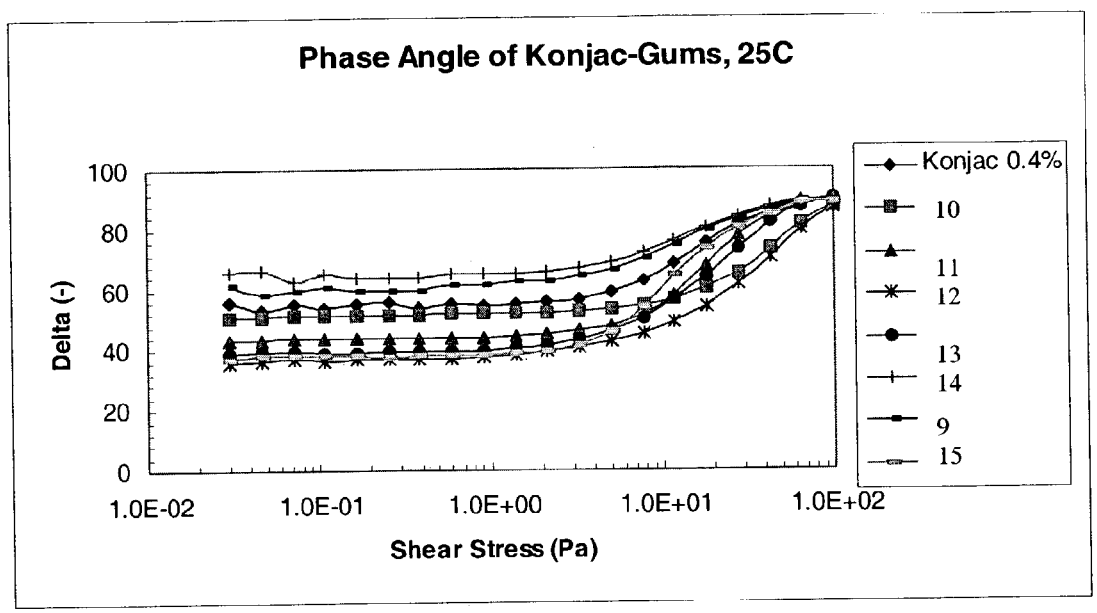
Figure 4A:
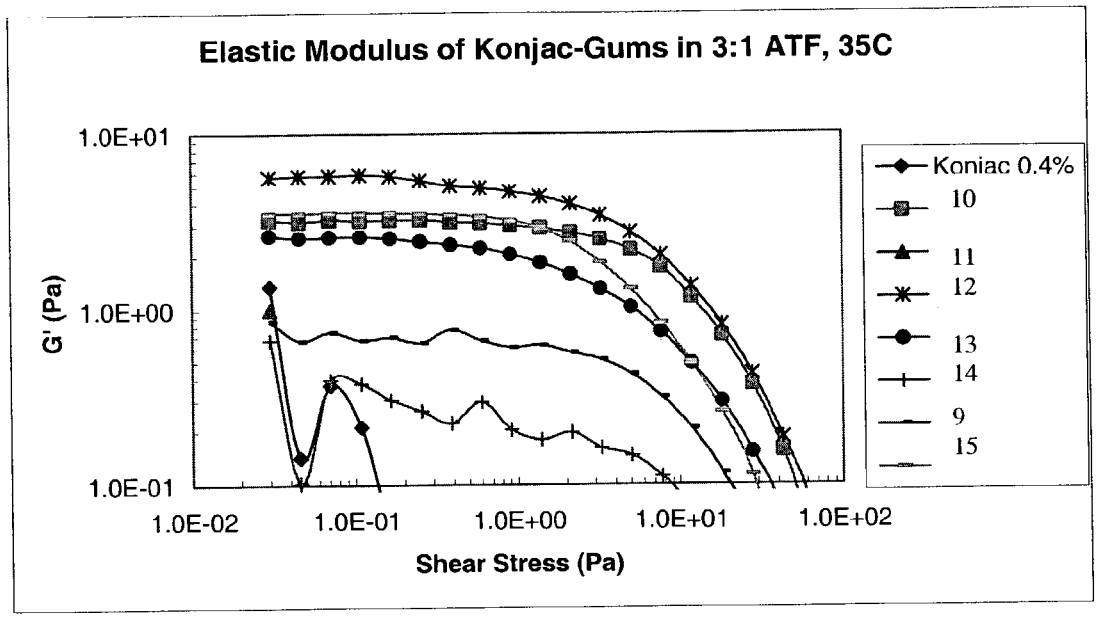
FIG. 4 is a set of three graphs illustrating the viseoelastic properties of Konjac combined with a variety of other gums in water mixed with ATF in a ratio of 3:1 at 35° C.: (a) elastic modulus, G', (b) viscous modulous, G", and (c) phase angle, δ, each as a function of applied shear stress. The composition of the gum solutions tested are given in Table 2.
Figure 4B:
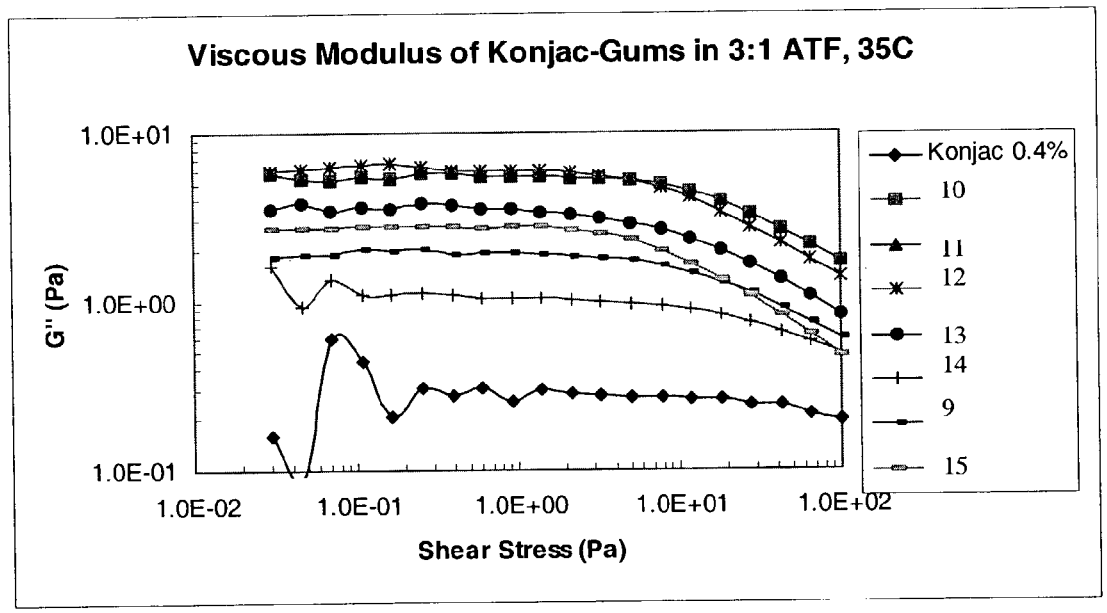
Figure 4C:
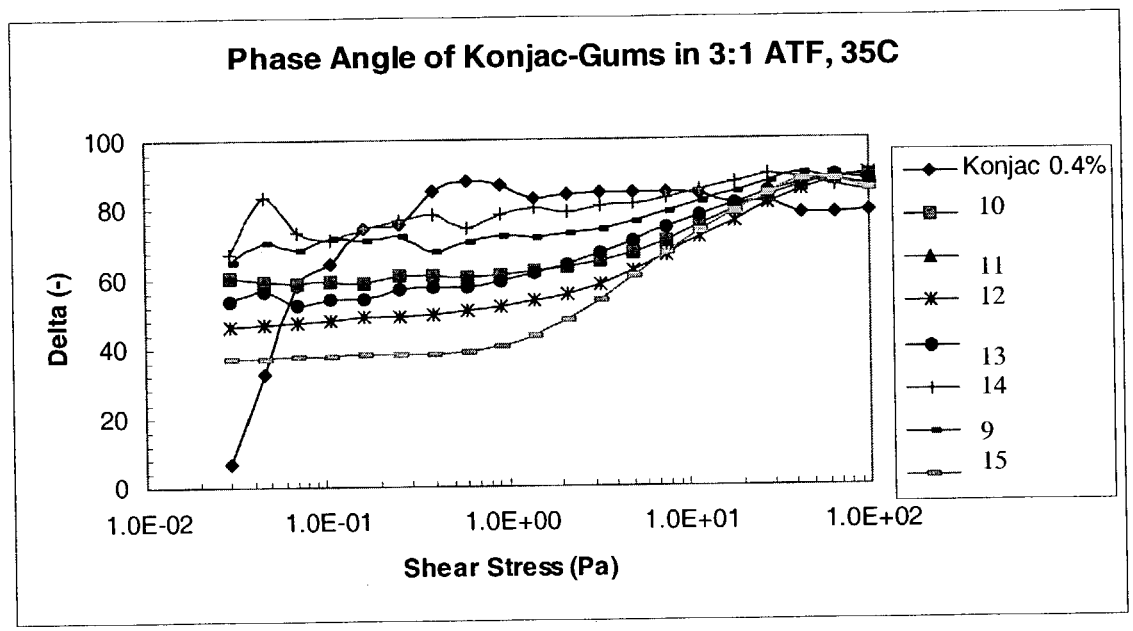

The following compositions were prepared in water along with 5% hydroxypropyl-β-cyclodextrin and 1% Linezolid. The results of the rheological tests are presented in FIGS. 3a–c, 4a–c.

TABLE 2

Combinations of Gums with Konjac. Summary of rheological and visual characterization.

| ID | Composition | Behavior at 25° C. | Behavior with 3:1 ATF at 35° C. |
|---|---|---|---|
| 9 | 0.5% Konjac | Thick viscoelastic fluid | Weak viscoelastic fluid |
| 10 | 0.25% Konjac 1% Sodium Alginate (high guluronic acid) | Thick viscoelastic gel Flows readily when shaken | Viscoelastic gel |
| 11 | 0.25% Konjac 0.5% HydroxyPropyl Guar | Thick viscoelastic gel More fluid after a few days at room temperature | Viscoelastic gel |
| 12 | 0.25% Konjac 1% PropyleneGlycol Alginate | Thick viscoelastic gel | Viscoelastic gel |
| 13 | 0.25% Konjac 0.4% Carbopol 971P | Thick viscoelastic gel Requires vigorous shaking to flow | Weak viscoelastic gel |
| 14 | 0.25% Konjac 1% Sodium Alginate | Viscoelastic fluid | Viscous fluid |
| 15 | 0.25% Konjac 0.4% Scelroglucan | Viscoelastic fluid Cloudy | Viscoelastic gel |

The results in Table 2 show that, while 0.5% konjac (ID# 9) remains a weak viscoelasic fluid, addition of other gels to only 0.25% konjac gives fair to good viscoelastic gels in the ATF test. Surprisingly, a great improvement is seen in the rheological characteristics of the formulation containing konjac and Carbopol 971P (ID# 13), compared to vehicles with either of the individual gels, as shown in Table 1, above. Similarly, the combination of konjac with scelroglucan (ID# 15) forms a viscoelastic gel in the ATF test, and the manufacturability of the combination is improved in comparison to a solution of scleroglucan, alone (compare to ID# 6 in Table 1).

Example 6

Combination of Gums with HydroxyPropyl Guar

Figure 5A:
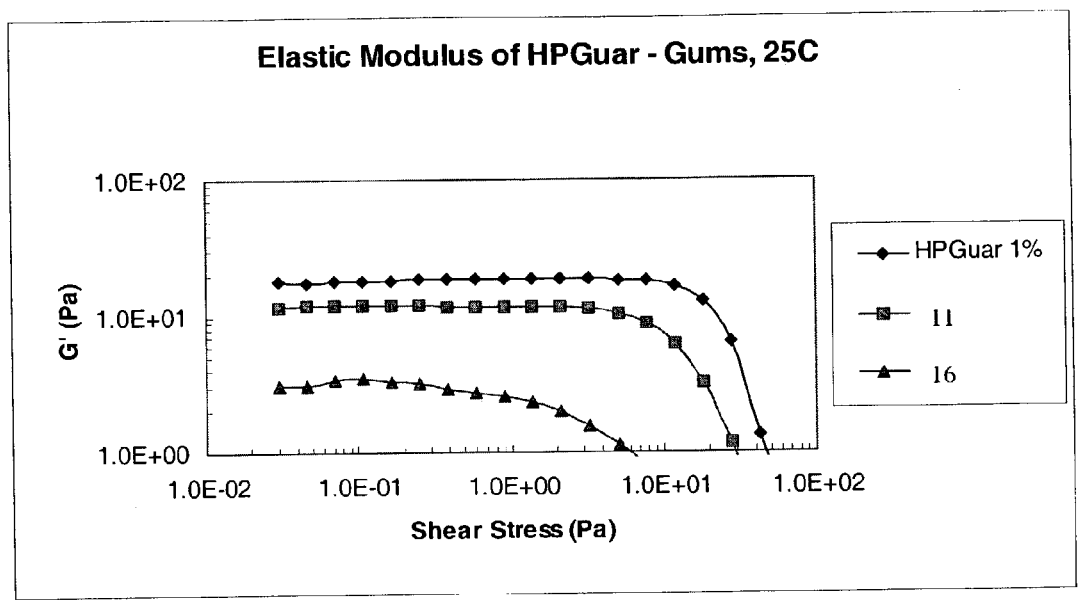
FIG. 5 is a set of three graphs illustrating the viseoelastic properties of HydroxyPropyl Guar combined with each of two other gums in water at 25° C.: (a) elastic modulus, G', (b) viscous modulous, G", and (c) phase angle, δ, each as a function of applied shear stress. The composition of the gum solutions tested are given in Table 3.
Figure 5B:
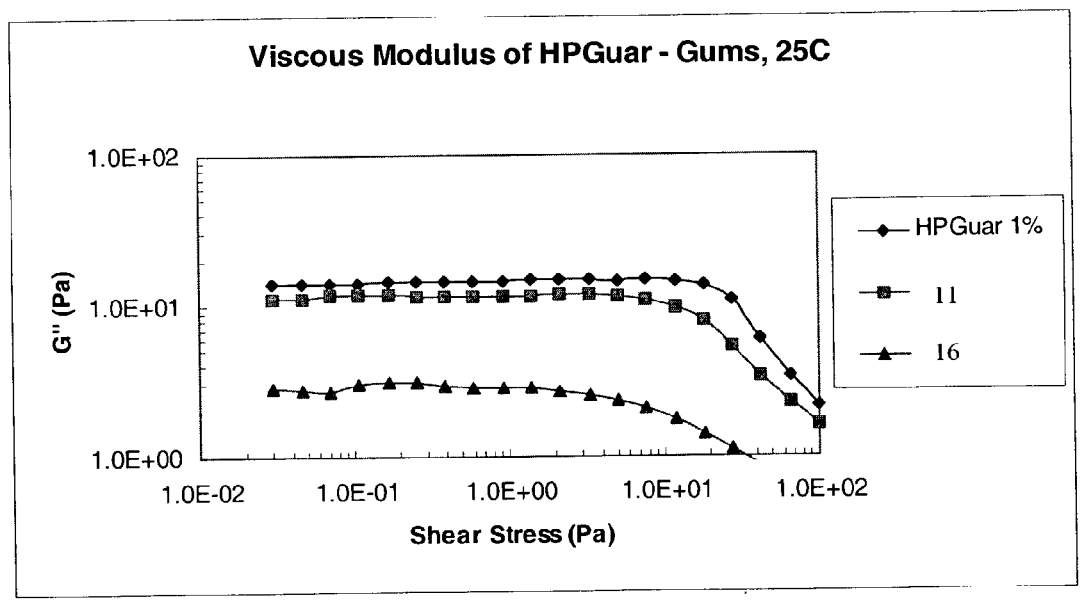
Figure 5C:
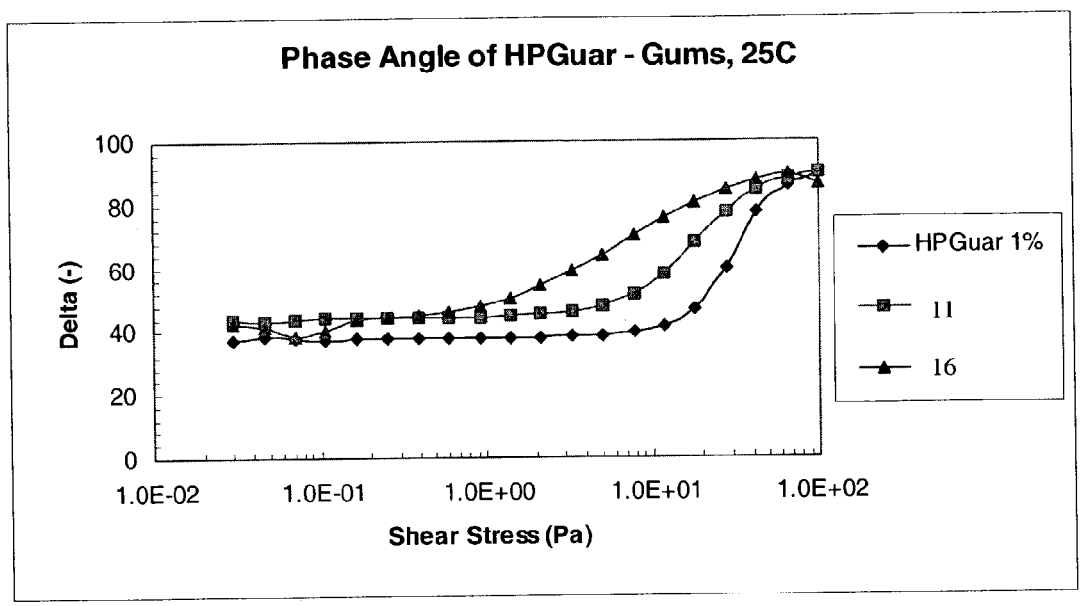
Figure 6A:
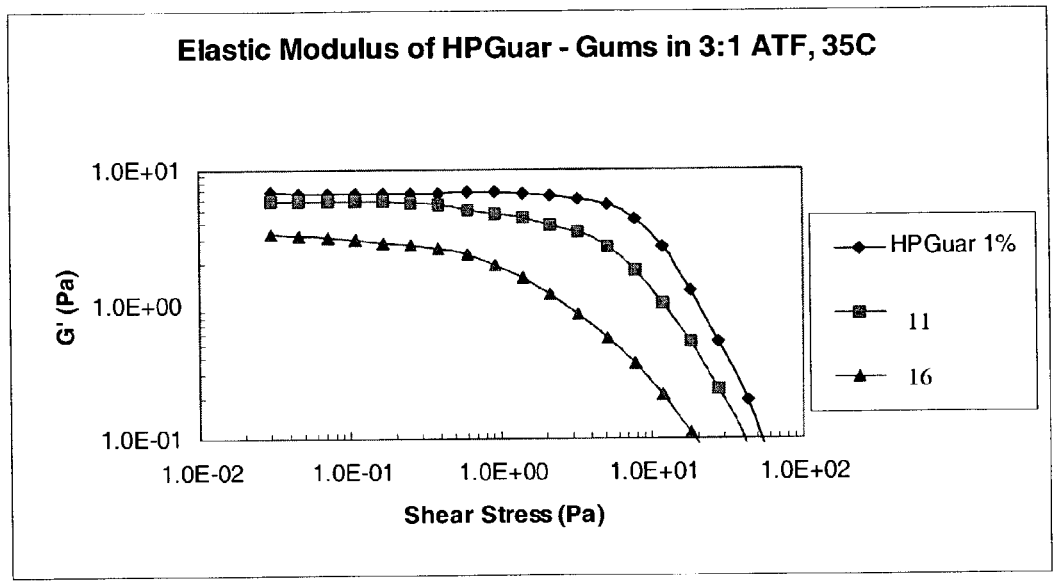
FIG. 6 is a set of three graphs illustrating the viseoelastic properties of HydroxyPropyl Guar combined with each of two other gums in water mixed with ATF in a 3:1 ratio at 35° C.: (a) elastic modulus, G', (b) viscous modulous, G", and (c) phase angle, δ, each as a function of applied shear stress. The composition of the gum solutions tested are given in Table 3.
Figure 6B:
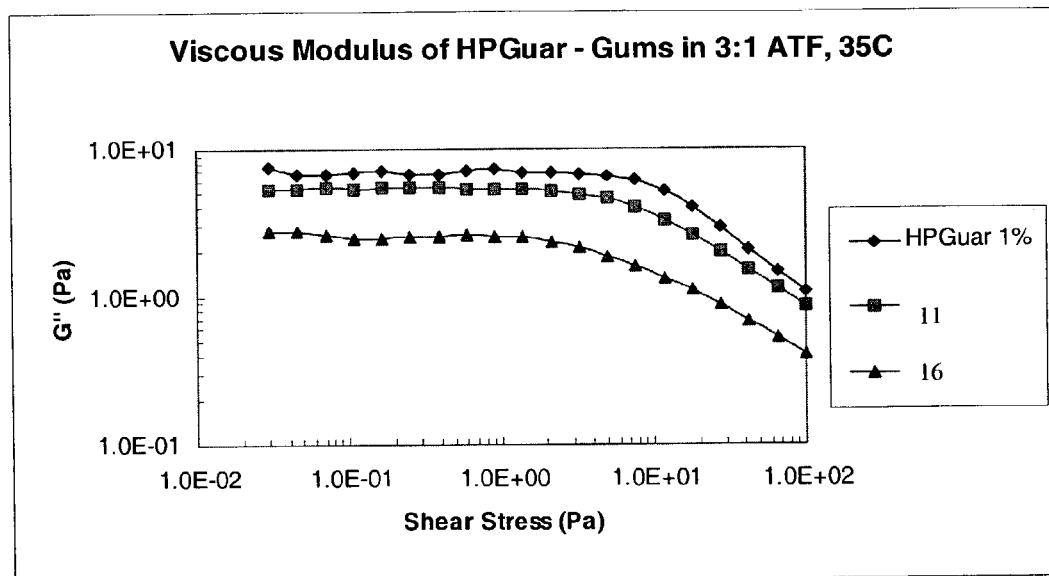
Figure 6C:
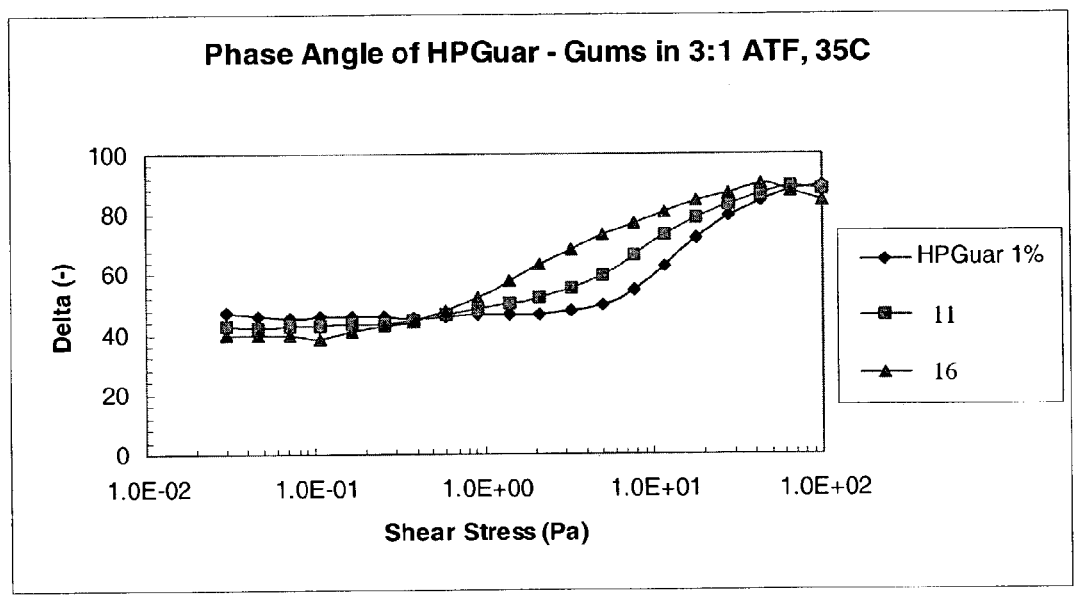

The following compositions containing hydroxypropyl guar or a combination of hydroxypropyl guar and other gums were prepared as described in Table 3, below, in water along with 5% HydroxyPropyl Beta Cyclodextrin and 1% Linezolid. Note that the first formulation described in Table 3, below (i.e., ID# 11), was first introduced in Table 2, above. Results of the Theological tests are presented in FIGS. 5a–c, 6a–c.

TABLE 3

Combinations of Gums with HydroxyPropyl Guar. Summary of rheological and visual characterization.

| ID | Composition | Behavior at 25° C. | Behavior with 3:1 ATF at 35° C. |
|---|---|---|---|
| 11 | 0.25% Konjac 05% HydroxyPropyl Guar | Thick viscoelastic gel More fluid after a few days at room temperature | Viscoelastic gel |

TABLE 3-continued

Combinations of Gums with HydroxyPropyl Guar. Summary of rheological and visual characterization.

| ID | Composition | Behavior at 25° C. | Behavior with 3:1 ATF at 35° C. |
|---|---|---|---|
| 16 | 0.5% HydroxyPropyl Guar 0.13% Agarose VII | Viscoelastic gel Flows readily when shaken | Weak viscoelastic gel |

Addition of Agarose to HydroxyPropyl Guar produces a fluid (ID# 19) which was found to be easily manufactured and filtered, compared to the combination of HydroxyPropyl Guar with Konjac (ID# 11). ID# 16, while not gelling as strongly as ID# 11, still produces a gel. Thus, on the basis of formulation and manufacturing properties and upon results illustrated in Table 2, above, addition of Agarose represents an improvement over addition of Konjac to HydroxyPropyl Guar.

Example 7

Combination of Gums with PropyleneGlycol Alginate

Figure 7A:
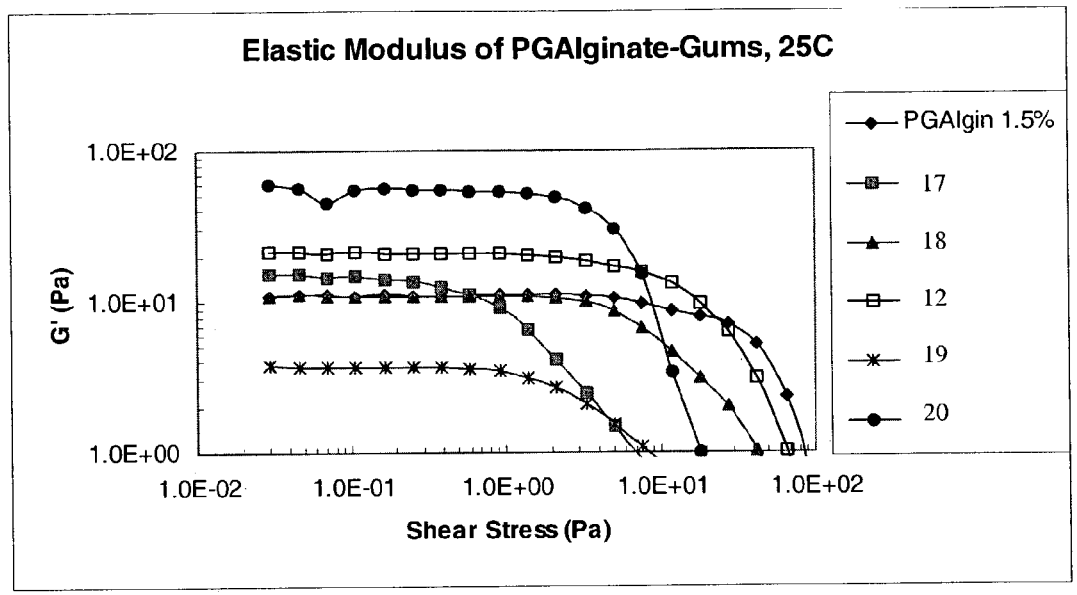
FIG. 7 is a set of three graphs illustrating the viseoelastic properties of PropyleneGlycol Alginate combined with various gums in water at 25° C.: (a) elastic modulus, G', (b) viscous modulous, G", and (c) phase angle, δ, each as a function of applied shear stress. The composition of the gum solutions tested are given in Table 4.
Figure 7B:
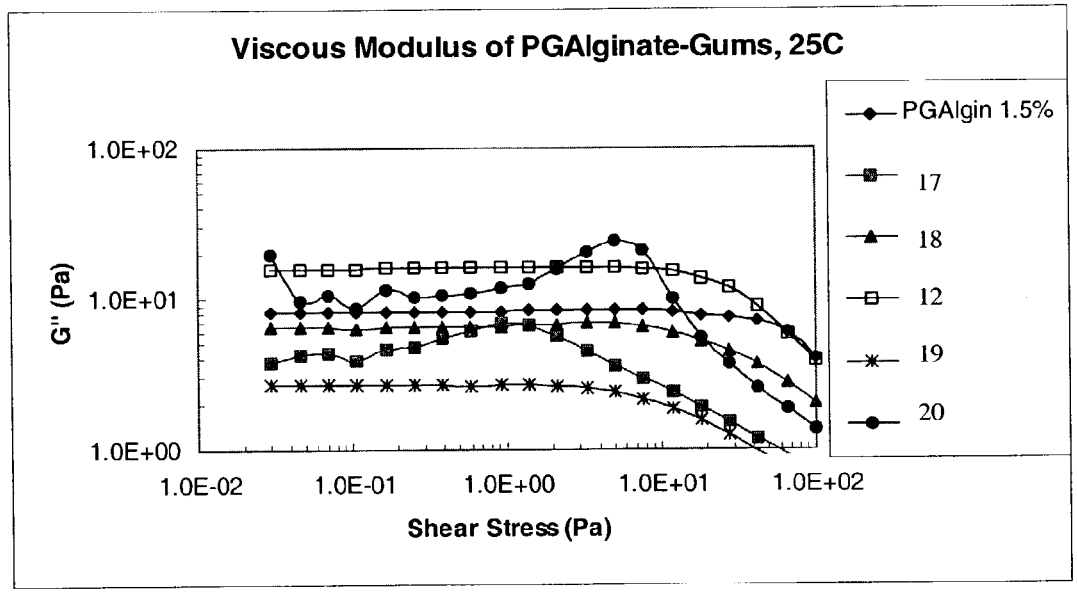
Figure 7C:
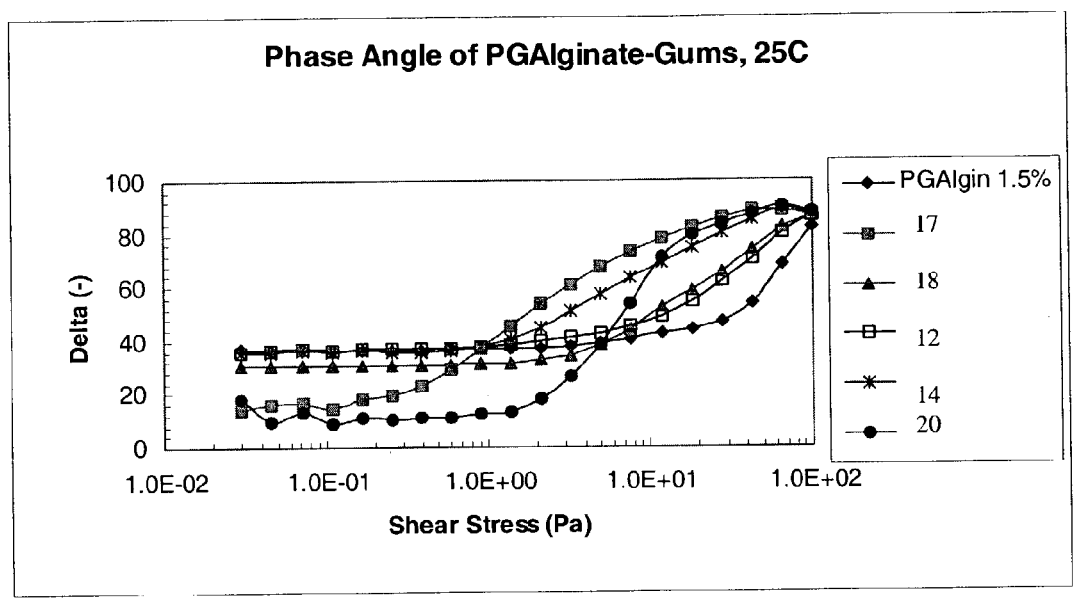
Figure 8A:
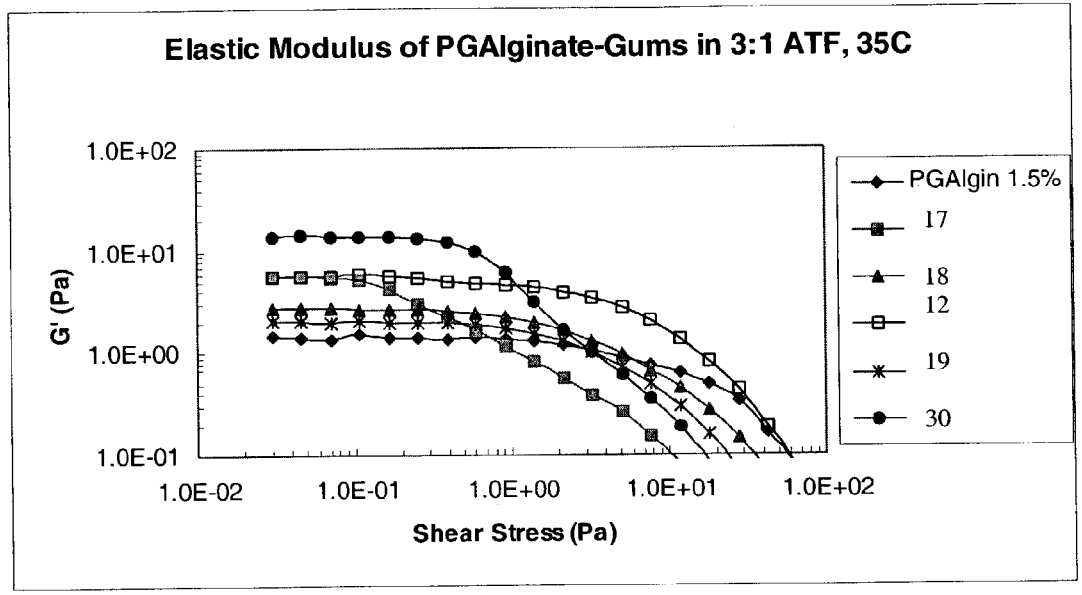
FIG. 8 is a set of three graphs illustrating the viseoelastic properties of PropyleneGlycol Alginate combined with various gums in water mixed with ATF in a ratio of 3:1 at 35° C.: (a) elastic modulus, G', (b) viscous modulous, G", and (c) phase angle, δ, each as a function of applied shear stress. The composition of the gum solutions tested are given in Table 4.
Figure 8B:
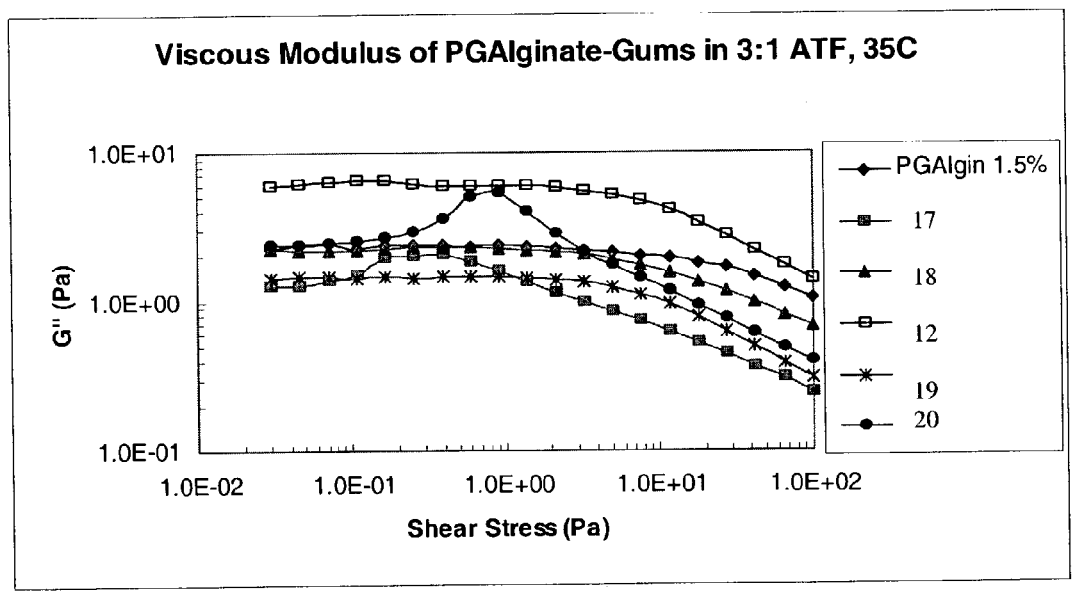
Figure 8C:
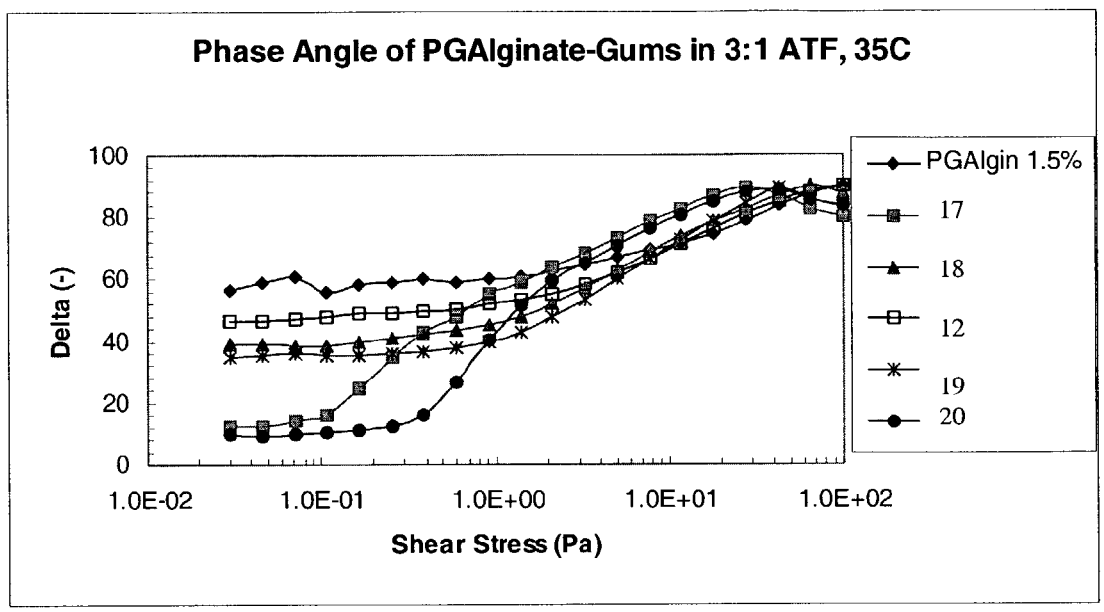

The following composition were prepared in water along with 5% HydroxyPropyl Beta Cyclodextrin and 1% Linezolid. The results of the rheological tests are presented in FIGS. 7a–c, 8a–c. A high viscosity grade of PropyleneGlycol Alginate was used.

TABLE 4

Combinations of Gums with PropyleneGlycol Alginate. Summary of rheological and visual characterization.

| ID | Composition | Behavior at 25° C. | Behavior with 3:1 ATF at 35° C. |
|---|---|---|---|
| 17 | 0.25% PropyleneGlycol Alginate 0.2% Agarose VII | Viscoelastic gel | Weak viscoelastic gel |
| 18 | 1% PropyleneGlycol Alginate 0.5% Scleroglucan | Viscoelastic gel Cloudy, Flows when shaken Settles quickly | Weak viscoelastic gel |
| 12 | 0.25% Konjac 1% PropyleneGlycol Alginate | Thick viscoelastic gel | Viscoelastic gel |
| 19 | 0.5% PropylenGlycol Alginate 0.3% Xanthan | Weak viscoelastic fluid | Viscoelastic fluid |
| 20 | 0.25% PropyleneGlycol Alginate 0.25% Agarose VII | Thick elastic gel | Viscoelastic gel |

The combinations, above, simply modulate the characteristics of a pure PropyleneGlycol Alginate vehicle (illustrated as ID# 5 in Table 1).

Example 8

Combination of Gums. Scieroglucan

Figure 9A:
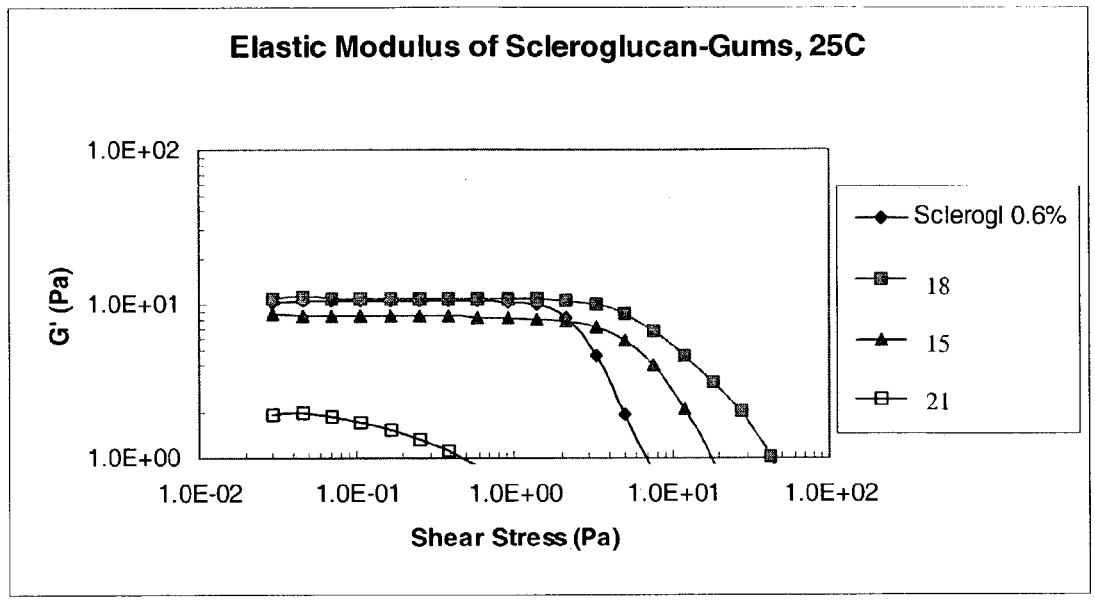
FIG. 9 is a set of three graphs illustrating the viseoelastic properties of Sclerogucan combined with each of three different gums in water at 25° C.: (a) elastic modulus, G', (b) viscous modulous, G", and (c) phase angle, δ, each as a function of applied shear stress. The composition of the gum solutions tested are given in Table 5.
Figure 9B:
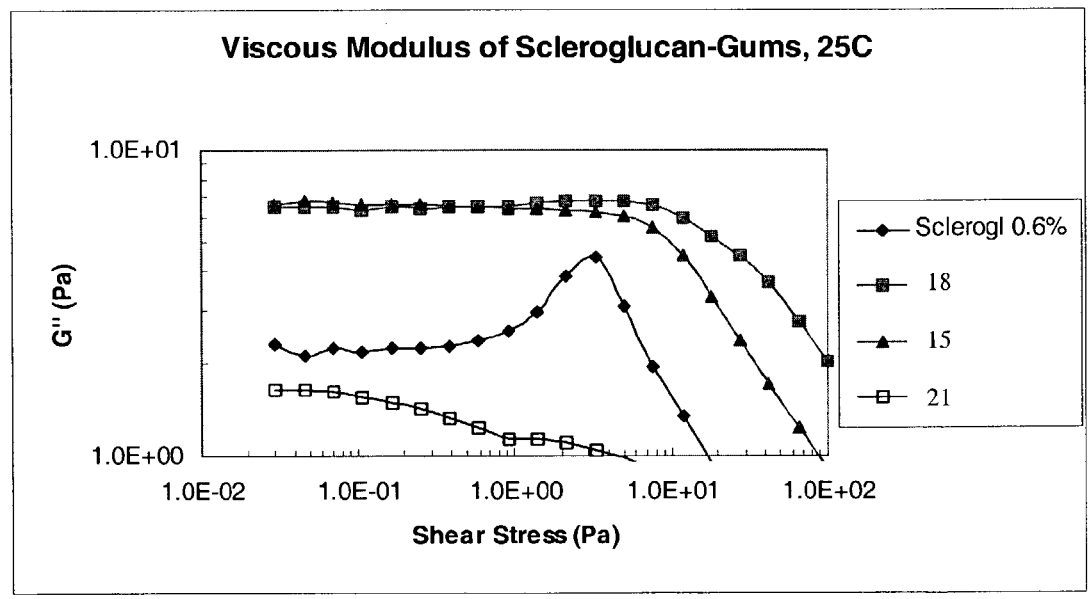
Figure 9C:
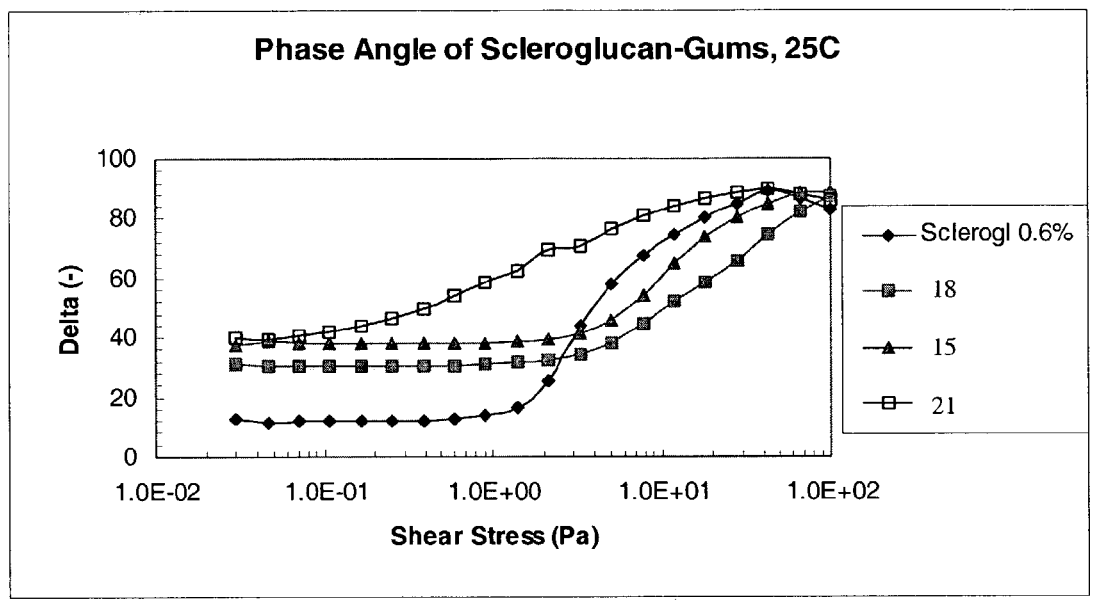
Figure 10A:
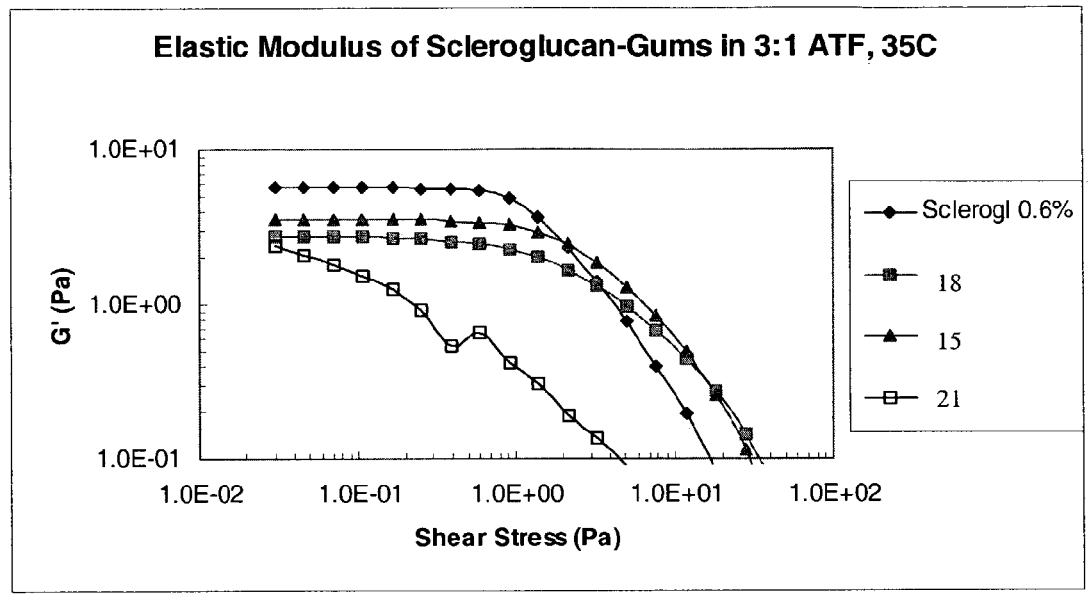
FIG. 10 is a set of three graphs illustrating the viscoelastic properties of Scleroglucan combined with each of three different gums in water mixed with ATF in a ratio of 3:1 at 35° C.: (a) elastic modulus, G', (b) viscous modulous, G", and (c) phase angle, δ, each as a function of applied shear stress. The composition of the gum solutions tested are given in Table 5.
Figure 10B:
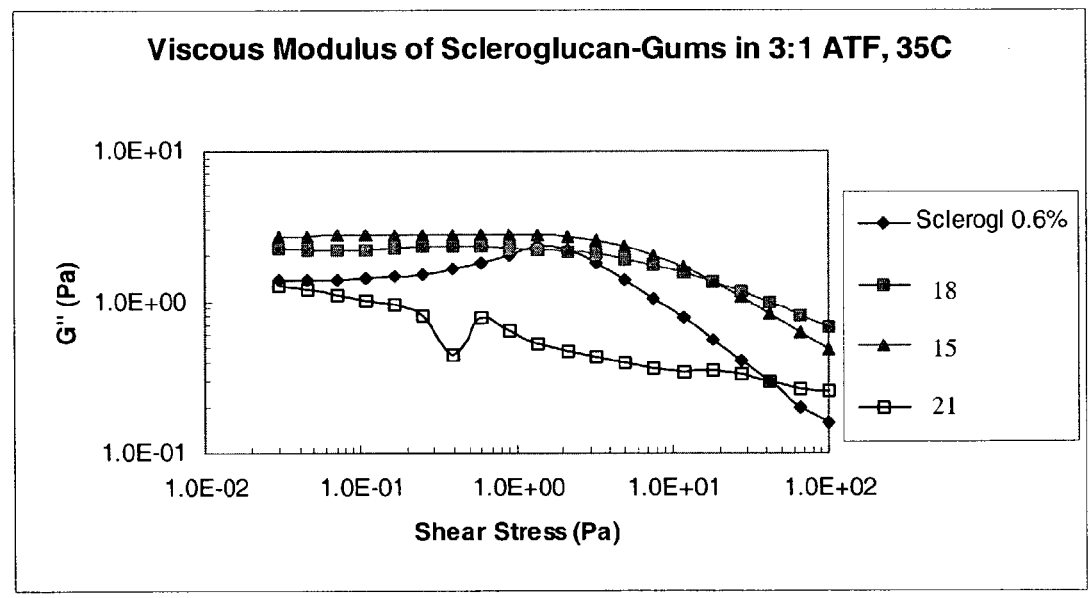
Figure 10C:
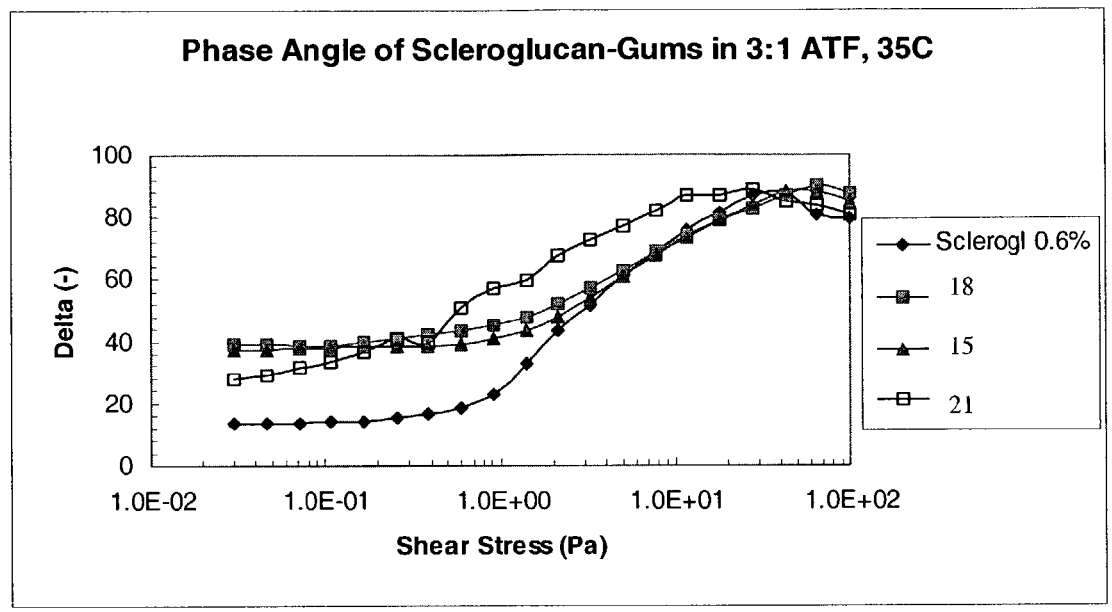

The following composition were prepared in water along with 5% HydroxyPropyl Beta Cyclodextrin and 1% Linezolid. The results of the rheological tests are presented in FIGS. 9a–c, 10a–c.

TABLE 5

Combinations of Gums with Scleroglucan. Summary of rheological and visual characterization.

| ID | Composition | Behavior at 25° C. | Behavior with 3:1 ATF at 35° C. |
|---|---|---|---|
| 18 | 1% PropyleneGlycol Alginate 0.5% Scleroglucan | Viscoelastic gel Cloudy, Flows when shaken Settles quickly | Weak viscoelastic gel |
| 20 | 0.25% Konjac 0.4% Scleroglucan | Viscoelastic gel Cloudy | Weak viscoelastic gel |
| 21 | 0.5% Scleroglucan 0.5% HydroxyPropyl Methyl Cellulose | Weak viscous fluid Cloudy | Weak viscoelastic fluid |

All of the scleroglucan gel combination formulations described in Table 5, above, showed gelling behavior in the ATF test. However, compared to Scleroglucan alone (See ID# 1 in Table 1), a more consistent viscoelastic gel behavior is obtained with any one of the additional gel species tested.

Example 9

Pharmokinetic and Tolerability Performance of Formulations

The following compositions were dosed to rabbits in the Drug Adsorption PK model, as described in Example 2, above. All formulations comprised 5% HydroxyPropyl Beta Cyclodextrin and 2% Mannitol and adjusted to a pH between about pH 4 and about pH 5, unless stated otherwise. No discomfort during dosing was observed during the studies, indicating that the formulations were well tolerated

TABLE 7

Reference formulations

| ID | Composition | Linezolid (%) | Concentration in Conjunctiva at 1 hr (μg/g) |
|---|---|---|---|
| A | Normal Saline | 0.25 (No Cyclodextrin) | 0.8 |
| E | 0.76% iota-Carrageenans | 0.25 (No Cyclodextrin) | 6.6 |
| E1 | 0.76% iota-Carrageenans | 1 | 34.2 |
| E3 | 0.48% Gellan Gum | 1 | 9.7 |

TABLE 8

Combinations of Gums with Konjac.

| ID | Composition | Linezolid (%) | Concentration in Conjunctiva at 1 hr (μg/g) |
|---|---|---|---|
| 9 | 0.5% Konjac | 0.05 | 1.06 (Theoretically 32 if drug at 1%) |
| 10 | 0.25% Konjac 1% Sodium Alginate (high guluronic acid) | 1 | 30.4 |
| 11 | 0.25% Konjac 0.5% HydroxyPropyl Guar | 1 | 14.25 |
| 12 | 0.25% Konjac 1% PropyleneGlycol Alginate | 1 | 18 |
| 13 | 0.25% Konjac 0.4% Carbopol 971P | 1 | 14.1 |

TABLE 8-continued

Combinations of Gums with Konjac.

| ID | Composition | Linezolid (%) | Concentration in Conjunctiva at 1 hr (μg/g) |
|---|---|---|---|
| 14 | 0.25% Konjac 1% Sodium Alginate | 0.05 | 1.6 (Theoretically 32 if drug at 1%) |
| 15 | 0.25% Konjac 0.4% Scelroglucan | 1 | 39.7 |

TABLE 9

Combinations of Gums with HydroxyPropyl Guar.

| ID | Composition | Linezolid (%) | Concentration in Conjunctiva at 1 hr (μg/g) |
|---|---|---|---|
| 11 | 0.25% Konjac 0.5% HydroxyPropyl Guar | 1 | 14.2 |
| 16 | 0.5% HydroxyPropyl Guar 0.13% Agarose VII | 1 | 18 |

TABLE 10

Combinations of Gums with PropyleneGlycol Alginate.

| ID | Composition | Linezolid (%) | Concentration in Conjunctiva at 1 hr (μg/g) |
|---|---|---|---|
| 17 | 0.25% PropyleneGlycol Alginate 0.2% Agarose VII | 1 | 26.4 |
| 18 | 1% PropyleneGlycol Alginate 0.5% Scleroglucan | 1 | 54.5 |
| 12 | 0.25% Konjac 1% PropyleneGlycol Alginate | 1 | 18 |
| 19 | 0.5% PropylenGlycol Alginate 0.3% Xanthan | 1 | 14.5 |
| 20 | 0.25% PropyleneGlycol Alginate 0.25% Agarose VII | 0.25 (No Cyclodextrin) | 10.7 |

TABLE 11

Combinations of Gums with Scleroglucan.

| ID | Composition | Linezolid (%) | Concentration in Conjunctiva at 1 hr (μg/g) |
|---|---|---|---|
| 18 | 1% PropyleneGlycol Alginate 0.5% Scleroglucan | 1 | 54.5 |
| 15 | 0.25% Konjac 0.4% Scleroglucan | 1 | 39.7 |
| 21 | 0.5% Scleroglucan 0.5% HydroxyPropyl Methyl Cellulose | 1 | 5.9 |

The results in Tables 7 through 11, above, illustrate that a significant enhancement of the amount of linezolid delivered to ocular tissue was achieved by each of the formulations with the combination of gums tested herein.

Example 10

Manufacture of Ophthalmic Compositions of Three Different Drugs

Ophthalmic compositions of three different drugs having low solubility in water are made, using a hydroxypropyl guar gum and agarose gum system and hydroxypropyl-β-cyclodextrin as a solubilizing agent. The compositions of each of the three formulations is given in Table 12, below.

TABLE 12

Combinations of Two Drugs with New Gum System

| Formulation # | Components | % by Weight |
|---|---|---|
| 22 | HydroxyPropyl Guar Gum | 0.5% |
|  | Agarose (medium gelling temperature) | 0.13% |
|  | Hydroxypropyl-β-cyclodextrin | 5% |
|  | Dextramethasone | 1% |
| 23 | HydroxyPropyl Guar Gum | 0.5% |
|  | Agarose (medium gelling temperature) | 0.13% |
|  | Hydroxypropyl-β-cyclodextrin | 0.5% |
|  | Diclofenac | 0.1% |

These two formulations are expected to have viscosity and gelation behavior in the eye similar to ID#16 in Table 9, as illustrated in Example 9, above.

What is claimed is:

1. A pharmaceutical composition suitable for topical administration to an eye, comprising: (a) a pharmacologically effective concentration of an active agent; and (b) a set of at least two ophthalmically compatible polymers selected from the group consisting of konjac and sodium alginate; konjac and hydroxy propyl guar; konjac and propylene glycol alginate; konjac and Carbopol 971; hydroxy propyl guar and agarose; propylene glycol alginate and agarose; and propylene glycol alginate and scleroglucan.

2. The pharmaceutical composition of claim 1, wherein the active agent is a steroid.

3. The pharmaceutical composition of claim 1 wherein the active agent is an NSAIDS compound.

4. The pharmaceutical composition of claim 1, wherein the active agent is an oxazolidinone antibiotic drug.

5. The pharmaceutical composition of claim 4 wherein the oxazolidinone antibiotic drug of a compound of formula (I): wherein: $R^1$ is selected from (a) H, (b) $C_{1-8}$ alkyl optionally substituted with at least one F, Cl, OH, $C_{1-8}$ alkoxy, and $C_{1-8}$ acyloxy or $C_{1-8}$ benzoxy, including a $C_{3-6}$ cycloalkyl group, (c) amino, (d) mono- and di($C_{1-8}$ alkyl)amino and (e) $C_{1-8}$ alkoxy groups; $R^2$ and $R^3$ are independently selected from H, F and Cl groups; $R^4$ is H or $CH_3$; $R^5$ is selected from H, $CH_3$, CN, $CO_2R^1$ and $(CH_2)_m R^6$ groups, where $R_1$ is as defined above, $R^6$ is selected from H, OH, $OR^1$, $OCOR^1$, $NHCOR^1$, amino, mono- and di($C_{1-8}$ alkyl)amino groups, and m is 1 or 2; n is 0, 1 or 2; and X is O, S, SO, $SO_2$, $SNR^7$ or $S(O)NR^7$ where $R^7$ is seleceted from H, $C_{1-4}$ alkyl (optionally substituted with one or more F, Cl, OH, $C_{1-8}$ alkoxy, amino, $C_{1-8}$ mono- or di($C_{1-8}$ alkyl)amino groups), and p-toluenesulfonyl groups; or a pharmaceutically acceptable salt thereof.

6. The pharmaceutical composition of claim 5 wherein, in formula (I), $R^1$ is $CH_3$; $R^2$ and $R^3$ are independently selected from H and F but at least one of $R^2$ and $R^3$ is F; $R^4$ and $R^5$ are each H; n is 1; and X is selected from O, S and $SO_2$ 7. The pharmaceutical composition of claim 4 wherein the oxazolidinone antibiotic drug is selected from the group consisting of: linezolid, eperezolid, N-((5S)-3-(3-fluoro-4-(4-(2-fluoroethyl)-3-oxopiperazin-1-yl)phenyl)-2-ox-oox-azolidin-5-ylmethyl-acetamide, (S)—N-[[3-[5-(3-pyridyl) thiomorphen-2-yl]-2-oxo-5-oxazolidinyl]methyl]acetamide, (S)—N-[[3-[5-(4-pyridyl)pyrid-2-yl]-2-oxo-5-oxazolidinyl] methyl]acetamide hydrochloride and N-[[(5S)-3-[4-(1,1-di-oxido-4-thiomorpholiny)-3,5-difluorophenyl]-2-oxo-5-ox-azoldinyl]methyl]acetamide.

8. The pharmaceutical composition of claim 4 wherein the oxazolidinone antimicrobial drug is linezolid.

9. The pharmaceutical composition of claim 1, further comprising a cyclodextrin compound in a concentration sufficient to ensure that essentially all of the active agent in the composition is in solution.

10. The pharmaceutical composition of claim 9 wherein the cyclodextrin compound is selected from the group consisting of α-cyclodextrin, β-cyclodextrin, γ-cyclodextrin, an alkylcyclodextrin, a hydroxyalkylcyclodextrin, a carboxyalkyl-cyclodextrin, and sulfoalkylether cyclodextrin.

11. The pharmaceutical composition of claim 9 wherein the cyclodextrin compound is selected from the group consisting of hydroxypropyl-β-cyclodextrin and sulfobu-tylether-β-cyclodextrin.

12. The pharmaceutical composition of claim 9 wherein the cyclodextrin concentration is about 1 mg/ml to about 500 mg/ml.

13. The pharmaceutical composition of claim 1, wherein the set of at least two ophthalmically compatible polymers reduces the rate of removal of the composition from the eye by lacrimation, such that a concentration of the active agent in lacrimal fluid of the eye is maintained above the MIC $_{90}$ for at least about 2 hours following topical application to the eye.

14. A method of treating and/or preventing a disease or infection in a an eye of a warm-blooded subject, the method comprising administering to the eye of the subject a therapeutically or prophylactically effective amount of the composition of claim 1.

15. A method of use of a composition of claim 1 in manufacture of a medicament for topically treating or preventing a disease or infection of an eye of a warm-blooded subject.

16. A pharmaceutical composition suitable for topical administration to an eye, comprising: (a) an oxazolidinone antimicrobial drug in a concentration effective for treatment and/or prophylaxis of a gram-positive bacterial infection of at least one tissue of the eye; (b) a pharmaceutically acceptable cyclodextrin compound in a cyclodextrin concentration sufficient to maintain the linezolid in solution; and (c) a set of at least two ophthalmically compatible polymers selected from the group consisting of konjac and sodium alginate; konjac and hydroxy propyl guar; konjac and propylene glycol alginate; konjac and Carbopol 971; hydroxy propyl guar and agarose; propylene glycol alginate and agarose; and propylene glycol alginate and scleroglucan.

17. The pharmaceutical composition of claim 16 wherein the oxazolidinone antibiotic drug of a compound of formula (I): 3wherein: $R^1$ is selected from (a) H, (b) $C_{1-8}$ alkyl optionally substituted with at least one F, Cl, OH, $C_{1-8}$ alkoxy, and $C_{1-8}$ acyloxy or $C_{1-8}$ benzoxy, including a $C_{3-6}$ cycloalkyl group, (c) amino, (d) mono- and di($C_{1-8}$ alkyl) amino and (e) $C_{1-8}$ alkoxy groups; $R^2$ and $R^3$ are independently selected from H, F and Cl groups; $R^4$ is H or $CH_3$; $R^5$ is selected from H, $CH_3$, CN, $CO_2R^1$ and $(CH_2)_mR^6$ groups, where $R^1$ is as defined above, $R^6$ is selected from H, OH, $OR^1$, $OCOR^1$, $NHCOR^1$, amino, mono- and di($C_{1-8}$ alkyl) amino groups, and m is 1 or 2; n is 0, 1 or 2; and X is O, S, SO, $SO_2$, $SNR^7$ or $S(O)NR^7$ where $R^7$ is selected from H, $C_{1-4}$ alkyl (optionally substituted with one or more F, Cl, OH, $C_{1-8}$ alkoxy, amino, $C_{1-8}$ mono- or di($C_{1-8}$ alkyl)amino groups), and p-toluenesulfonyl groups; or a pharmaceutically acceptable salt thereof.

18. The pharmaceutical composition of claim 17 wherein, in formula (I), $R^1$ is $CH_3$; $R^2$ and $R^3$ are independently selected from H and F but at least one of $R^2$ and $R^3$ is F; $R^4$ $R^5$ each H; n is 1; and X is selected from O, S and $SO_2$.

19. The pharmaceutical composition of claim 17 wherein the oxazolidinone antibiotic drug is selected from the group consisting of: linezolid, eperezolid, N-((5S)-3-(3-fluoro-4-(4-(2-fluoroethyl)-3-oxopiperazin-1-yl)phenyl)-2-ox-oox-azolidin-5-ylmethyl)-acetamide, (S)—N-[[3-[5-(3-pyridyl) thiophen-2-yl]-2-oxo-5-oxazolidinyl]methy]acetamide, (S)—N-[[3-[5-(4-pyridyl)pyrid-2-yl]-2-oxo-5-oxazolidinyl] methyl]acetamide hydrochloride and N-[[(5S)-3-[4-(1,1-dioxido-4-thiomorpholiny)-3,5-difluorophenyl]-2-oxo-5-oxazoldinyl]methyl]acetamide.

20. The pharmaceutical composition of claim 17 wherein the oxazolidinone antimicrobial drug is linezolid.

21. The pharmaceutical composition of claim 20, wherein the linezolid concentration is about 0.01 mg/ml to about 100 mg/ml.

22. The pharmaceutical composition of claim 16 wherein the cyclodextrin compound is selected from the group consisting of β-cyclodextrin, β-cyclodextrin, β-cyciodextrin, an alkylcyclodextrin, a hydroxyalkylcyclodextrin, a carboxyalkylcyclodextrin, and sulfoalkylether cyclodextrin.

23. The pharmaceutical composition of claim 16 wherein the cyclodextrin compound is selected from the group consisting of hydroxypropyl-β-cyclodextrin and sulfobu-tylether-β-cyclodextrin.

24. The pharmaceutical composition of claim 16 wherein the cyclodextrin compound is present at a concentration of about 1 mg/ml to about 500 mg/ml.

* * * * *